(12) United States Patent
Jacobs et al.

(10) Patent No.: US 7,431,929 B2
(45) Date of Patent: Oct. 7, 2008

(54) USE OF VACCINIA VIRUS DELETED FOR THE E3L GENE AS A VACCINE VECTOR

(75) Inventors: Bertram Jacobs, Tempe, AZ (US); Sangeetha Vijaysri, San Diego, CA (US); James Jancovich, Tempe, AZ (US); Latha Talasela, Phoenix, AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 11/022,477

(22) Filed: Dec. 22, 2004

(65) Prior Publication Data

US 2006/0008470 A1    Jan. 12, 2006

Related U.S. Application Data

(63) Continuation of application No. PCT/US03/21764, filed on Jul. 11, 2003.

(60) Provisional application No. 60/399,815, filed on Jul. 31, 2002, provisional application No. 60/397,907, filed on Jul. 24, 2002.

(51) Int. Cl.
*A61K 39/285* (2006.01)
*C12N 7/01* (2006.01)
*C12N 15/863* (2006.01)

(52) U.S. Cl. ............... 424/199.1; 435/235.1; 435/320.1

(58) Field of Classification Search ..................... None
See application file for complete search history.

(56) References Cited

U.S. PATENT DOCUMENTS

| | | | |
|---|---|---|---|
| 6,004,777 A | 12/1999 | Tartaglia et al. | |
| 6,372,455 B1 * | 4/2002 | Jacobs et al. | 435/69.1 |
| 6,750,043 B2 * | 6/2004 | Jacobs et al. | 435/69.3 |
| 6,846,652 B2 * | 1/2005 | Jacobs et al. | 435/69.3 |
| 6,942,855 B2 * | 9/2005 | Jacobs et al. | 424/93.2 |
| 2002/0028195 A1 | 3/2002 | Coffey et al. | |
| 2002/0155529 A1 | 10/2002 | Jacobs et al. | |
| 2003/0044384 A1 | 3/2003 | Roberts et al. | |

FOREIGN PATENT DOCUMENTS

| | | |
|---|---|---|
| WO | WO 92/12240 | 7/1992 |
| WO | WO 9955910 | 11/1999 |
| WO | WO 00/00216 * | 1/2000 |
| WO | WO 0062735 | 10/2000 |
| WO | WO 0073487 | 12/2000 |
| WO | WO 01/35970 A1 | 5/2001 |
| WO | WO 02/086059 * | 10/2002 |
| WO | WO 2004/003562 A2 | 1/2004 |

OTHER PUBLICATIONS

NCBI locus Q91S30. 2001. Obtained from the Internet Jul. 19, 2007 URL: <http://www.ncbi.nlm.nih.gov/entrez/viewer.fcgi?db=protein &id<81964299>.*

Beattie et al. 1995. Reversal of the Interferon-Sensitive Phenotype of a Vaccinia Virus Lacking E3L by Expression of the Reovirus S4 Gene. J. Virol. 69(1):499-505.

Beattie et al., 2006. Host-range restriction of vasccinia virus E3L-specific deletion mutants. Virus Genes. 12(1):89-94.

Brandt TA, Jacobs BL. Both carboxy- and amino-terminal domains of the vaccinia virus interferon resistance gene, E3L, are required for pathogenesis in a mouse model. J Virol. Jan. 2001;75(2):850-6.

Chang et al. 1992. The E3L gene of vaccinia virus encodes an inhibitor of the interferon-induced, doubled-stranded RNA-dependent protein kinase. PBAS. 89 :4825-4829.

Chang et al. 1993. Identification of a Conserved Motif that is necessary for binding of the vaccinia virus E3L gene protucts to double-stranded RNA. Virology. 194:537-547.

Chang et al. 1995. Rescue of Vaccina Virus Lacking the E3L Gene by Mutants of E3L. J. Virol. 69(10):6605-6608.

Kibler et al., 1997. Double-stranded RNA is a trigger for apoptosis in vaccinia virus-infected cells. J. Virol. 71(3):1992-2003.

Langland JO, Cameron JM, Heck MC, Jancovich JK, Jacobs BL. Inhibition of PKR by RNA and DNA viruses. Virus Res. Jul. 2006:119(1):100-10.

McInnes et al. Orf Virus Encodes a Homolog of the Vaccinia Virus interferon-resistance gene E3L. Virus Genes 17(2):107-115.

Rosenthal et al. Developing New Smallpox Vaccines. Emerging Infectious Diseases vol. 7 No. 6, Nov.-Dec. 2001.

Shors et al. 1997. Complementation of vaccinia virus deleted of the E3L gene by mutants of E3L gene by mutants of E3L. Virology 239:269-276.

Vijaysri S, Talasela L, Mercer AA, Mcinnes CJ, Jacobs BL, Langland JO. The Orf virus E3L homologue is able to complement deletion of the vaccinia virus E3L gene in vitro but not in vivo. Virology. Sep. 15, 2003;314(1):305-14.

Xiang, Y, Condit RC, Vijaysri S, Jacobs B, Williams BR, Silverman RH. Blockade of interferon induction and action by the E3L double-stranded RNA binding proteins of vaccinia virus. J Virol. May 2002;76(10):5251-9.

(Continued)

*Primary Examiner*—Mary E Mosher
(74) *Attorney, Agent, or Firm*—Womble Carlyle Sandrige & Rice, PLLC

(57) ABSTRACT

The present invention relates to vaccines having an increased level of safety comprising recombinant vaccinia viruses containing an inactivated E3L region. The invention also relates to methods for stimulating a protective immune response in an immunized host using the vaccines of the invention. The invention is based on the discovery that vaccinia virus mutants having deletions in the E3L region exhibit dramatically reduced pathogenesis while remaining highly immunogenic. In addition, the invention relates to modified recombinant vaccinia viruses engineered to express heterologous polypeptides and the use of such viruses in vaccines designed to stimulate a protective immune response against such polypeptides in a host. The invention further relates to an interferon-sensitive recombinant vaccinia virus with broad host range wherein a salamander eIF2α is inserted into the viral genome in place of at least a portion of the E3L gene.

6 Claims, 21 Drawing Sheets

OTHER PUBLICATIONS

Xiang Y, et al. 2001. Vaccinia virus E3L suppresses the IFN system by preventing activation of antiviral enzymes and IRF3 phosphorylation. J. Interferon Cytokine Research. 24(s1)S70-S71.

Lee et al. "The Interferon-induced double stranded RNA-activated protein kinase induces apoptosis" *Virology*, vol. 199, pp. 491-196, 1994.

\* cited by examiner

```
ATV      --MAHNRFYSEILPKQGDVTMCRVLSQSDSWDBGVYVSMMEYGNVKGYVAIGVENHRDIR 58
K3L      -----MLAFCYSLPNAGDVIKGRVYEK----DYALYIYLFDYPHSEAILAESVKMHMDRY 51
Human    MPGLSCRFYQHKFPEVEDVVMVNVRSIA---EMGAYVSLLEYNNIEGMILLSELSRRRIR 57
                :*:   **   .*       :  .*: :::* : :. :   .    :

ATV      KRFRKLAPGAEMCMTVLRVDREKGYVDLDDRPVNSNQAYECCSRYQLRRTEMAVAERAAE 118
K3L      VEYRDKLVGKTVKVKVIRVDYTKGYIDVN---------YKRMCRHQ-------------- 88
Human    SINKLIRIGRNECVVVIRVDKEKGYIDLSKRRVSPEEAIKCEDKFTKSKTVYSILRHVAE 117
             :    *    : *:***  ***:*:.         :   :.

ATV      YAGVKGSAVYDFLDETVRALIPGSLMSG---------------TKGLKISSDLKQLLK 161
K3L      -----------------------------------------------------------
Human    VLEYTKDEQLESLFQRTAWVFDDKYKRPGYGAYDAFKHAVSDPSILDSLDLNEDEREVLI 177

ATV      EFGAEVGLDRAGRAEAVVRVPGAFFGHVLRGVTNAYDAMKEMKPDSGVNVAVYPPERGVV 221
K3L      -----------------------------------------------------------
Human    NNINRRLTPQAVKIRADIEVACYGYEGIDAVKEALRAGLNCSTENMPIKINLIAPPRYVM 237

ATV      AVTVMA--------------GDSEAAYWGLHAVLFKVREVVKAAGGGLCPFV------- 259
K3L      -----------------------------------------------------------
Human    TTTTLERTEGLSVLSQAMAVIKEKIEEKRGVFNVQMEPKVVIDTDETELARQMERLEREN 297

ATV      ------------------
K3L      ------------------
Human    AEVDGDDDAEEMEAKAED 315
```

USE OF VACCINIA VIRUS DELETED FOR THE E3L GENE AS A VACCINE VECTOR

CROSS REFERENCE TO RELATED APPLICATIONS

This application claims priority to the following applications: International Patent Application No. PCT/US2003/021764 filed on Jul. 11, 2003 and published under International Publication No. WO 2003/009763 on Jan. 29, 2004, of which the instant application is a continuation application, and the provisional applications to which International Patent Application No. PCT/US2003/021764 also claims priority, namely, U.S. Provisional Patent Application No. 60/397,907 filed on Jul. 24, 2002 and U.S. Patent Provisional Application No. 60/399,815, filed on Jul. 31, 2002 each of which are incorporated by reference in their entireties herein.

GRANT SUPPORT

The subject matter of this application was supported at least in part by grant No. IBN 9977063GR from The National Science Foundation, so that the U.S. Government has certain rights herein.

INTRODUCTION

The present invention relates to vaccines having an increased level of safety comprising recombinant vaccinia viruses containing an inactivated E3L region. The invention further relates to methods for stimulating a protective immune response in an immunized host using the vaccines of the invention. The invention is based on the discovery that vaccinia virus mutants having deletions in the E3L region exhibit dramatically reduced pathogenesis while remaining highly immunogenic. In addition, the invention relates to modified recombinant vaccinia viruses engineered to express heterologous polypeptides and the use of such viruses in vaccines designed to stimulate a protective immune response against such polypeptides in a host.

BACKGROUND

Vaccinia virus is a member of the poxvirus family of DNA viruses. Vaccinia virus has been used successfully to immunize against smallpox, resulting in worldwide eradication of smallpox. Many different strains of vaccinia virus exist and the different strains demonstrate varying degrees of immunogenicity and are implicated with a variety of different complications, such as post-vaccinial encephalitis and generalized vaccinia. Thus, the use of vaccinia virus recombinants as expression vectors and particularly as vaccines and anticancer agents raises safety concerns associated with introducing live recombinant viruses into the environment.

Poxviruses including vaccinia virus are used extensively as expression vectors since the recombinant viruses are relatively easy to isolate, have a wide host range, and can accommodate large amounts of DNA. The vaccinia virus genome contains nonessential regions into which exogenous DNA can be incorporated. Exogenous DNA has been inserted into the vaccinia virus genome using well-known methods of homologous recombination. The basic technique of inserting foreign genes into live infectious poxvirus involves recombination between pox DNA and homologous plasmid DNA bearing the gene of interest (see, for example, U.S. Pat. No. 6,372,455). DNA molecules (e.g., plasmids, naked DNA, viral vectors, and poxviruses) have been used for insertion and expression of foreign genes. The resulting recombinant vaccinia viruses are useful as vaccines and anticancer agents.

A critical objective in vector development is to create a so called "attenuated vector" for enhanced safety, so that the vector may be employed in an immunological or vaccine composition. Thus, a balance between the efficiency and the safety of a vaccinia virus-based recombinant vaccine is extremely important. The recombinant virus must present the immunogen(s) in a manner that elicits a protective immune response in the vaccinated host but lacks any significant pathogenic properties. Virulence of vaccinia virus recombinants in a variety of host systems has been attenuated by the deletion or inactivation of certain vaccinia virus genes that are nonessential for virus growth. Replication-competent strains of vaccinia virus currently used against smallpox are interferon-resistant (Thacore and Younger, 1973, Virology 56:505-11).

Type I interferons are induced upon viral infection and constitute an integral part of the host cell's antiviral response (Samuel, 2001, *Clin Microbiol Rev* 14(4):778-809, table of contents). Double-stranded RNA (dsRNA), which is produced during most viral infections, but otherwise absent from cells, is believed to directly activate human interferon regulatory factor 3 (IRF-3; from an inactive state), thereby triggering transcriptional activation of IFN (Wathelet et al., 1998, *Mol Cell* 1(4):507-18; Lin et al., 1998, *Mol Cell Biol* 19:2986-96; Sato et al., 1998, *FEBS Lett* 452:112-16; Weaver et al., 1998, *Mol Cell Biol* 18:1359-68; Yoneyama et al., 1998, *EMBO J.* 17:1087-95; (Nguyen et al., 1997, *Cytokine Growth Factor Rev* 8(4):293-312). The rate-limiting step in this process is C-terminal phosphorylation of IRF-3 by an uncharacterized virus activated kinase (VAK) activity (Servant et al., 2001, *J Biol Chem* 276(1):355-63).

Two of the best characterized IFN-induced proteins are the dsRNA dependent enzymes, PKR and 2'-5' oligo adenylate synthetase (OAS) (Jacobs and Langland, 1996, *Virology* 219(2):339-49). PKR is a protein kinase consisting of an amino-terminal dsRNA-binding domain and a carboxy-terminal catalytic domain and is activated by autophosphorylation in a process mediated by dsRNA (Bryan, 1999, *Oncogene* 18:6112-6120; Clemens and Ella, 1997, *J Interferon Cytokine Res* 17(9):503-24). Following activation, PKR phosphorylates various substrates including the α subunit of protein synthesis initiation factor 2, eIF-2α (Samuel, 1979, *Proc Natl Acad Sci USA* 76(2):600-4). Phosphorylation of eIF-2α inhibits translation in general by impairing the eIF-2B-catalyzed guanine nucleotide exchange reaction (Clemens and Elia, 1997, *J Interferon Cytokine Res* 17(9):503-24). Thus, this inhibition blocks viral replication at the level of protein synthesis (Gale, 1998, *Mol Cell Biol* 18(2):859-71).

Activated OAS polymerizes ATP to produce 2'-5' linked oligoadenylates (Rebouillat and Hovanessian, 1999, *J Interferon Cytokine Res* 19(4):295-308). These oligoadenylates subsequently activate a potent antiviral enzyme, RNase L, which cleaves single-stranded RNAs (Baglioni et al., 1979, *Biochemistry* 18(9), 1765-70; Silverman and Cirino, 1997, *Gene Regulation* (Morris, D. R., Hartford, J. B., eds), 295-309, John Wiley & Sons). IFN treatment of cells elevates the level of OAS and RNase L but these proteins remain enzymatically inactive until dsRNA is produced upon viral infection (Sen, 2000, *Semin Cancer Biol* 10(2):93-101). Both PKR and OAS activation result in an inhibition of viral, and at times, host protein synthesis (Jacobs and Langland, 1996, *Virology* 219(2):339-49).

Both PKR and OAS are targets of viral systems that attempt to defeat host cell resistance. For example, the vaccinia virus (VV) E3L and K3L gene products inhibit PKR (Clemens and Elia, 1997, *J Interferon Cytokine Res* 17(9):503-24). The viral E3L protein is a dsRNA-binding protein that blocks autoactivation of PKR by sequestering dsRNA activators of PKR (Shors et al., 1997, *Virology* 239(2):269-76) and possibly interacting directly with the eIF-2α-binding region of PKR (Sharp et al., 1998, *Virology* 250(2):302-15). E3L is a potent inhibitor not only of the PKR kinase, but also of OAS (Rivas et al., 1998, *Virology* 243(2):406-14). The E3L gene encodes two related proteins, p20 and p25 (Chang et al., 1992, *Proc Natl Acad Sci USA* 89(11):4825-9; Yuwen et al., 1993, *Virology* 195(2):732-44). These gene products are early viral proteins containing a dsRNA-binding motif and are required for providing interferon resistance to the virus (Watson et al., 1991, *Virology* 185:206-16; Chang et al., 1992, *Proc Natl Acad Sci USA* 89(11):4825-9; Kibler et al., 1997, *J Virol* 71(3):1992-2003).

The VV E3L gene products consist of amino-terminal and carboxy-terminal domains, separated by a trypsin-sensitive spacer region (Ho and Shuman, 1996, *Virology* 217(1):272-84). The C terminal domain contains one copy of a conserved dsRNA-binding motif and is required for dimerization of the protein. Mutational analysis demonstrates that the C-terminal domain is required for dsRNA binding and PKR inhibitory activity seen in VV infected cells (Chang and Jacobs, 1993, *Virology* 194(2):537-47; Ho and Shuman, 1996, *J Virol* 70(4): 2611-4).

The N-terminal domain of E3L shares significant sequence homology with the eukaryotic RNA-editing enzyme ADAR1, which catalyzes the deamination of adenosine residues that are present in dsRNA, or in secondary structures of predominantly ssRNA (Patterson et al., 1995, *Virology* 210(2):508-11). The amino-terminal 45% of EM, upstream of the dsRNA-binding domain, is not essential for replication of vaccinia virus in several different cell lines in culture (Kibler et al., 1997, *J Virol* 71(3):1992-2003; Shors et al., 1997, *Virology* 239(2):269-76). The amino terminus of E3L proteins has also been reported to directly interact with the catalytic domain of PKR, suggesting that this interaction may be required for the function of E3L protein (Romano et al., 1998, *Mol Cell Biol* 18(12):7304-16). The E3L gene products are the only VV gene products known to localize to both the nucleus and cytoplasm of infected cells (Yuwen et al., 1993, *Virology* 195(2):732-44; Chang et al., 1995, *J Virol* 69(10): 6605-8). Sequences at the amino-terminus of E3L are necessary for accumulation of E3L products in the nucleus. These results suggest that cytoplasmic, but not nuclear, accumulation of the E3L gene products is required for efficient viral replication in cells in culture.

The E3L gene also confers a broad host range to VV enabling it to replicate in several cell types including HeLa, Vero and L cells (Chang et al., 1995, *J Virol* 69(10):6605-8; Shors et al., 1997, *Virology* 239(2):269-76). Deletion of the E3L gene from vaccinia virus produces a recombinant virus that is interferon-sensitive and highly debilitated for replication in cells in culture (Jacobs and Langland, 1996, *Virology* 219:339-49). VV deleted of the E3L gene (VVΔE3L) has a severely reduced host-range phenotype in that it does not replicate in human HeLa, and monkey kidney COS, CV-1, or BSC-40 cells, even in the absence of IFN treatment (Beattie et al., 1996, *Virus Genes* 12(1), 89-94). Interferon sensitivity is exemplified by VVΔE3L's sensitivity to pretreatment of rabbit kidney RK-13 cells with IFN-β and its inability to rescue Vesicular Stomatitis Virus from the effects of IFN (Shors et al., 1998, *Virology* 239(2):269-76).

VVΔE3L infection induces apoptosis in HeLa cells in an IFN-independent manner (Lee and Esteban, 1994, *Virology* 199(2):491-6; Kibler et al., 1997, *J Virol* 71(3):1992-2003). VVΔE3L infection also induces apoptosis in IFN-treated RK-13 cells (Kibler et al., 1997, *J Virol* 71(3):1992-2003). Infection with VVΔE3L leads to activation of PKR and increased phosphorylation of eIF2α (Beattie et al., 1995, *Virology* 210(2), 254-63; Beattie et al., 1995, *J Virol* 69(1), 499-505) in HeLa cells irrespective of IFN treatment, and in IFN-treated RK-13 cells. Infection of several cells with VVΔE3L leads to rRNA degradation typical of activation of the OAS/RNase L pathway (Beattie et al., 1995, *J Virol* 69(1), 499-505). Thus, both PKR-mediated and OAS-mediated antiviral defense mechanisms are active in cells infected with VVΔE3L.

It has been shown that recombinant vaccinia viruses in which the E3L gene is replaced by a gene encoding an E3L homolog from the orf virus, a poxvirus of the genus parapoxvirus that infects sheep, goats and humans, are immunogenic but have decreased pathogenicity in mice relative to wild-type vaccinia virus (U.S. Pat. No. 6,372,455). When administered intranasally, these recombinant viruses replicated to high titers in nasal tissues, but did not spread to the lung or brain and had reduced neurovirolence.

Development of enhanced vectors having enhanced transcription and/or expression which are attenuated continues to be a desirable goal, especially since attenuation may raise expression levels and/or persistence. Thus, there remains a need in the art for the development of vectors that have reduced pathogenicity while maintaining immunogenicity.

The iridoviruses are large DNA viruses that share many features of replication with the poxviruses, including cytoplasmic transcription and DNA synthesis (Jacobs, 2000, *Translational control CH* 35, 1-21 (CSHL Press)). They encode an eIF2α homolog (Yu et al., 1999, *Virus Res* 63(1-2):53-63). Essbauer et al., 2001 have analyzed the eIF2α of several iridoviruses of fish and frogs (*Virus Genes* 23(3):347-59). eIF2α homologous sequences of European catfish virus (ECV I-III), European sheatfish virus (ESV), and frog virus-3 (FV-3) had a length of 780 nucleotides. At the N-terminus (amino acid 1-100), the iridoviral eIF2α showed a significant homology to the N-termini of cellular initiation factor 2-α of various species and full-length poxyiral K3L protein. The eIF2α iridoviral protein had 37% identity with and 48% similarity to the N-terminus of human eIF2α and 32% identity with and 48% similarity to the K3L protein of VV. Several sites were highly conserved in all eukaryotic, iridoviral and poxyiral proteins. Serine 51 of cellular eIF2α, which is phosphorylated by PKR, could not be found in any viral proteins. At amino acids 15-89, the iridovirus protein reveals a homology to the S1 domain of ribosomal proteins (Bycroft et al., 1997, *Cell* 88(2):235-42). The C-terminus of the iridoviral proteins (amino acid 100-end) has no homology to any known protein (Essbauer et al., 2001, *Virus Genes* 23(3):347-59).

The homology of poxyiral and iridoviral proteins does not include 19 residues that flank serine phosphorylation site 51 and that are perfectly conserved from yeast to humans. The pentapeptide KGYID motif, which is important for the interaction of K3L of VV with the PKR is modified to KGYVD in all iridoviral eIF2α amino acid sequences. Since the C-terminus of ranaviral eIF2α reveals no homology to any known protein, it remains unclear whether a truncated form (N-terminal 100 amino acids) of the iridovirus protein could be functional and also why these polypeptides are longer than their poxviral homologs (Essbauer et al., 2001, *Virus Genes* 23(3):347-59). Thus, it is unclear whether the iridovirus homolog is acting as an eIF2α kinase inhibitor, or given its large size, as an alternative eIF2α-like translation initiation factor.

*Ambystoma tigrinum* virus (ATV) is a member of the genus ranavirus in the family Iridoviridae, which was isolated from diseased tiger salamanders (*Ambystoma tigrinum stebbinsi*). ATV genome sequencing has yielded the sequence of a gene with homology to the eukaryotic translation initiation factor, eIF2α. The role of this gene, if any, in ATV's ability to suppress antiviral host cell responses had not previously been determined.

SUMMARY OF THE INVENTION

The present invention provides vaccines comprising a recombinant vaccinia virus from which the region encoding the E3L gene product has been inactivated and a suitable carrier. The recombinant vaccinia virus of the invention may comprise exogenous DNA. This exogenous DNA may encode a gene product. A nonlimiting example of gene products that may be encoded is a polypeptide, e.g., an epitope to which a protective immune response is desired. Another nonlimiting example of a gene product that may be encoded is a ribonucleic acid or polypeptide bearing some desirable property.

In some embodiments of the invention, vectors having reduced pathogenicity while maintaining immunogenicity have been prepared. Recombinant vaccinia viral vectors were prepared wherein the E3L gene was replaced by the eIF2α gene from ATV. The recombinant virus is interferon sensitive, but possesses a broad host range; is able to inhibit the PKR pathway but not the OAS pathway and IRF-3 phosphorylation. Without being limited to any particular mechanism of action, these results indicate that the ATV eIF2α homolog acts as a novel PKR inhibitor by causing proteolytic degradation of PKR and it provides the salamander virus, ATV, with a novel gene to counteract host defenses. The compositions of the invention are useful for eliciting an immune response to smallpox virus and other molecules.

BRIEF DESCRIPTION OF THE DRAWINGS

FIG. 9. Comparison of amino acid sequence of ATV eIF2α (SEQ ID NO:1), vaccinia virus K3L (SEQ ID NO:2), and human eIF2α (SEQ ID NO:3). Alignment was performed using Clustal W 1.81. Stars indicate conserved amino acid residues.

Figure 18:
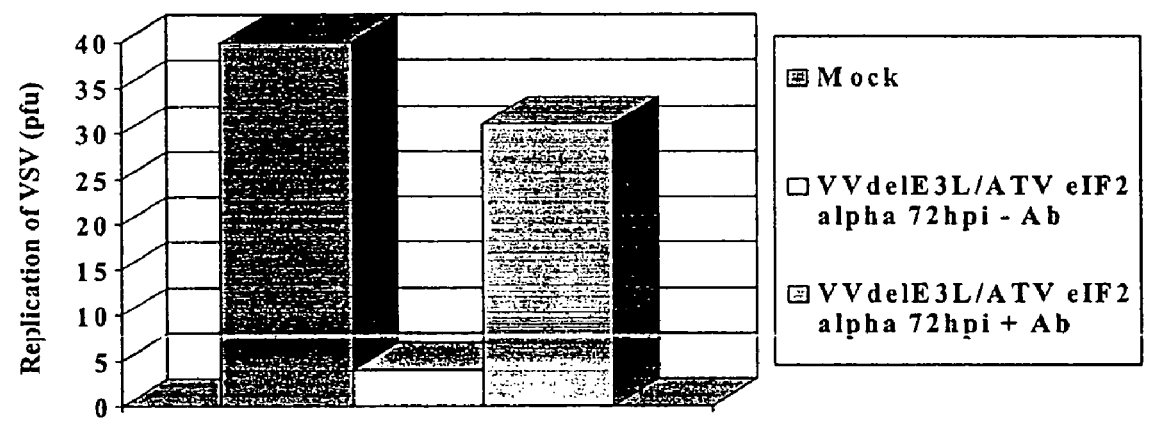

FIG. 18. Rescue of VSV. HeLa cells were mock treated or treated with cultured supernatant from the multi-step growth curve in the presence or absence of anti IFN-α antibody as described in material sand methods and infected with VSV 18 hours post treatment. 24 hpi cells were stained with neutral red and the number of plaques of VSV were counted to test the ability of VSV to grow under the gien conditions and shown as replication of VSV in pfu's on the Y-axis.

Figure 19:
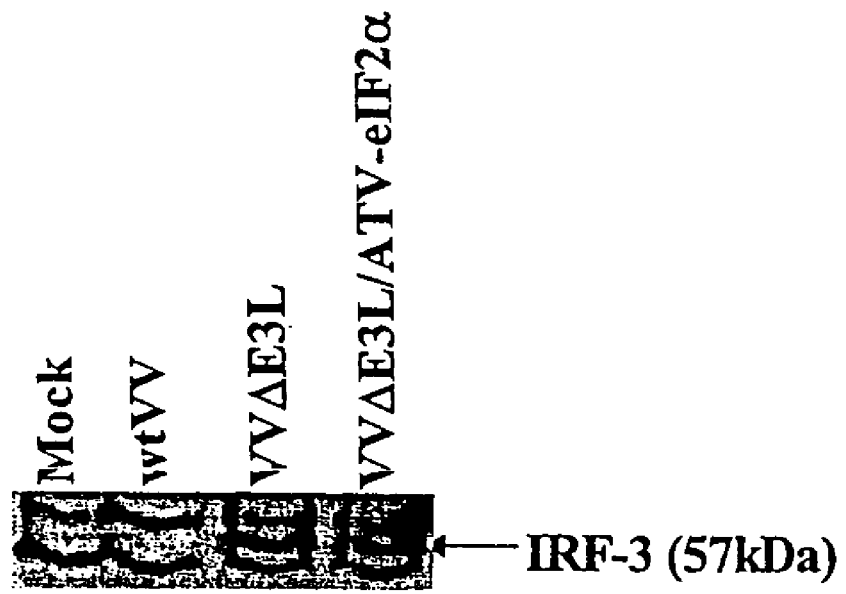

FIG. 19. IRF-3 phosphorylation. HeLa cells were mock infected or infected with wtVV, VVΔE3L, or VVΔE3L/ATV eIF2α at a moi of 5 and harvested at 6 hpi. Nuclear extracts were prepared and run on a 10% SDS-PAGE gel, transferred onto nitrocellulose, and probed with anti-IRF-3 antibody. Blots were analyzed by chemiluminescence.

Figure 20:
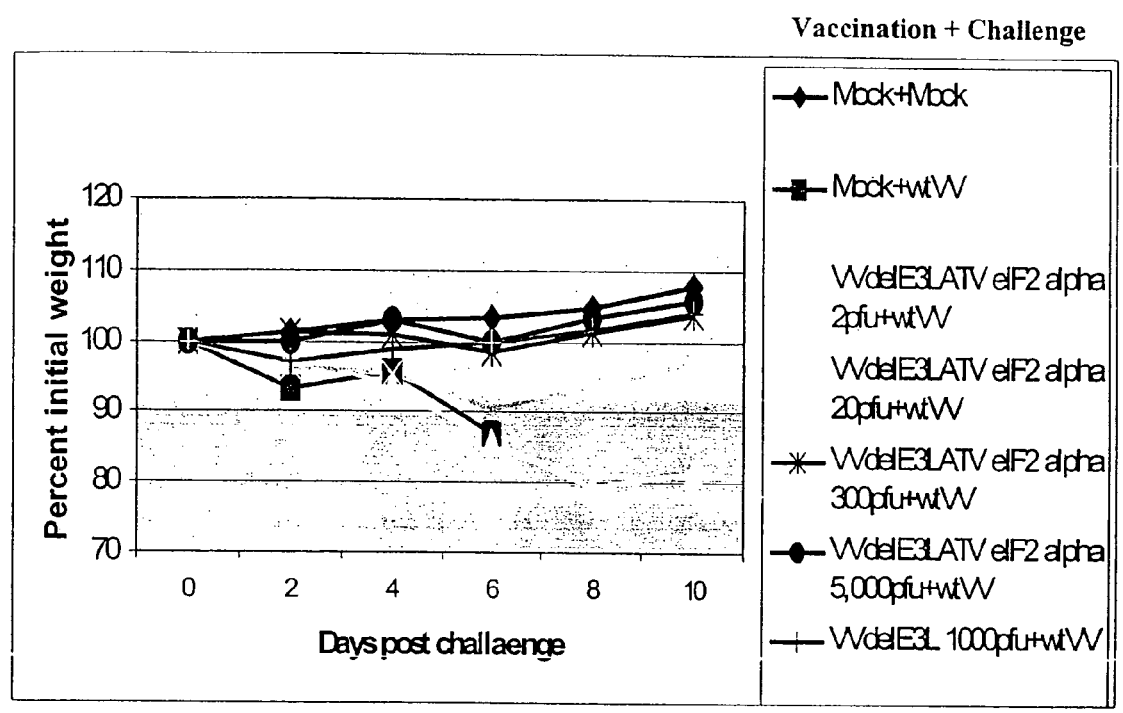

FIG. 20. Weight loss on Challenging Mice Vaccinated with VVΔE3L/ATV eIF2α.

Figure 21:
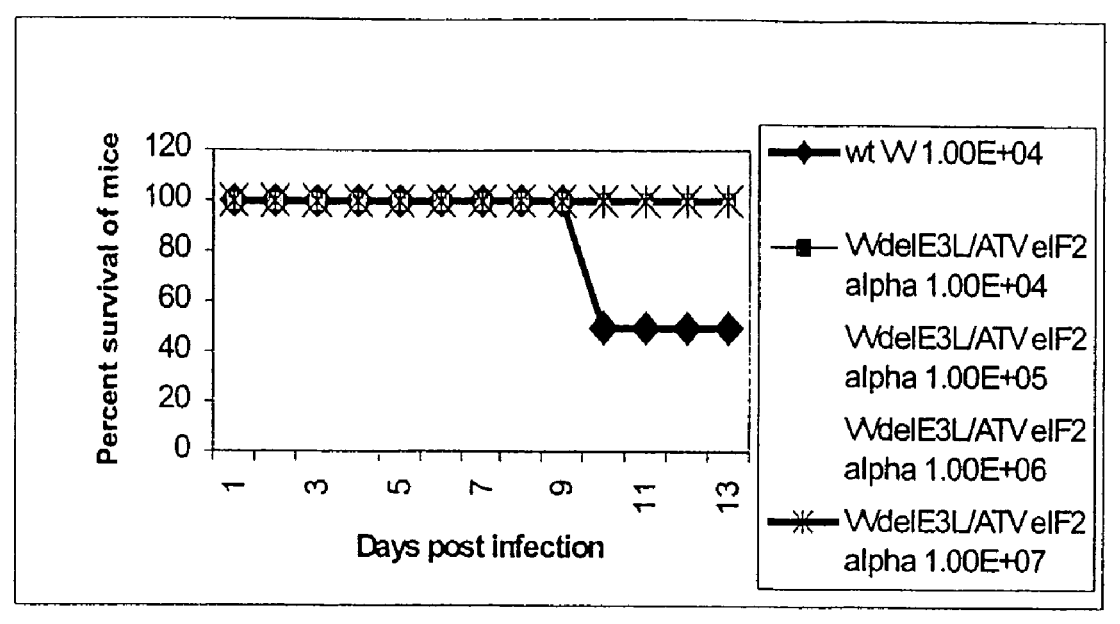

FIG. 21. Survival of Mice Following Intranasal Infection with VVΔE3L/ATV eIF2α.

DETAILED DESCRIPTION OF THE INVENTION

The present invention provides vaccines comprising a recombinant vaccinia virus from which the region encoding the E3L gene product has been inactivated. Such inactivation may result from partial or complete deletion of the E3L region or, alternatively, substitution of nucleotides within the E3L region that result in inactivation of the E3L gene product.

The E3L gene product of the vaccinia virus is a 190 amino acid polypeptide. The E3L gene codes for several functions including a dsRNA-binding protein, a Z-DNA-binding protein, and dimerization. Amino acids 118-190 have been implicated in dsRNA binding, as disclosed by Chang and Jacobs (1993, *Virology* 194:537-547). Amino acid numbering as used herein is adopted from Goebel et al., 1990, *Virology* 179:247-66, 577-63.

According to the invention "deletion of the E3L gene" and its grammatical equivalents refer to a vaccinia virus wherein a nucleic acid encoding all 190 amino acids or a subset of the 190 amino acids of E3L are not present. According to the invention, if the vaccinia virus having a deletion in the E3L gene has a residual nucleic acid encoding a subset of the 190 amino acids of E3L, said residual nucleic acid is incapable of producing a functional gene product or the gene product is incapable of binding dsRNA. The ability of the E3L gene product to bind to dsRNA can be determined by binding assays known in the art and disclosed, for example, by Chang et al., 1993, Virology 194:537.

According to the invention, "recombinant vaccinia virus" refers to a vaccinia virus having a deletion or, alternatively, nucleotide substitutions in the E3L gene. The term includes vaccinia virus wherein a heterologous nucleic acid is substituted for the E3L gene.

Replication-competent strains of vaccinia virus currently used for vaccination against smallpox are interferon-resistant (Thacore and Younger, 1973, Virol. 56(2):505-511). Deletion of the E3L gene from vaccinia virus results in a virus that is interferon-sensitive, but also is highly debilitated for replication in many cells in culture (Jacobs and Langland, 1996, *Virolology* 219(2):339-349). This virus is also dramatically less virulent in both immune competent (FIGS. 1 and 2 and Brandt and Jacobs, 2001, *J Virol* 75(2): 850-6) and immune suppressed (FIG. 3) mice than wild type vaccinia virus.

Figure 4:
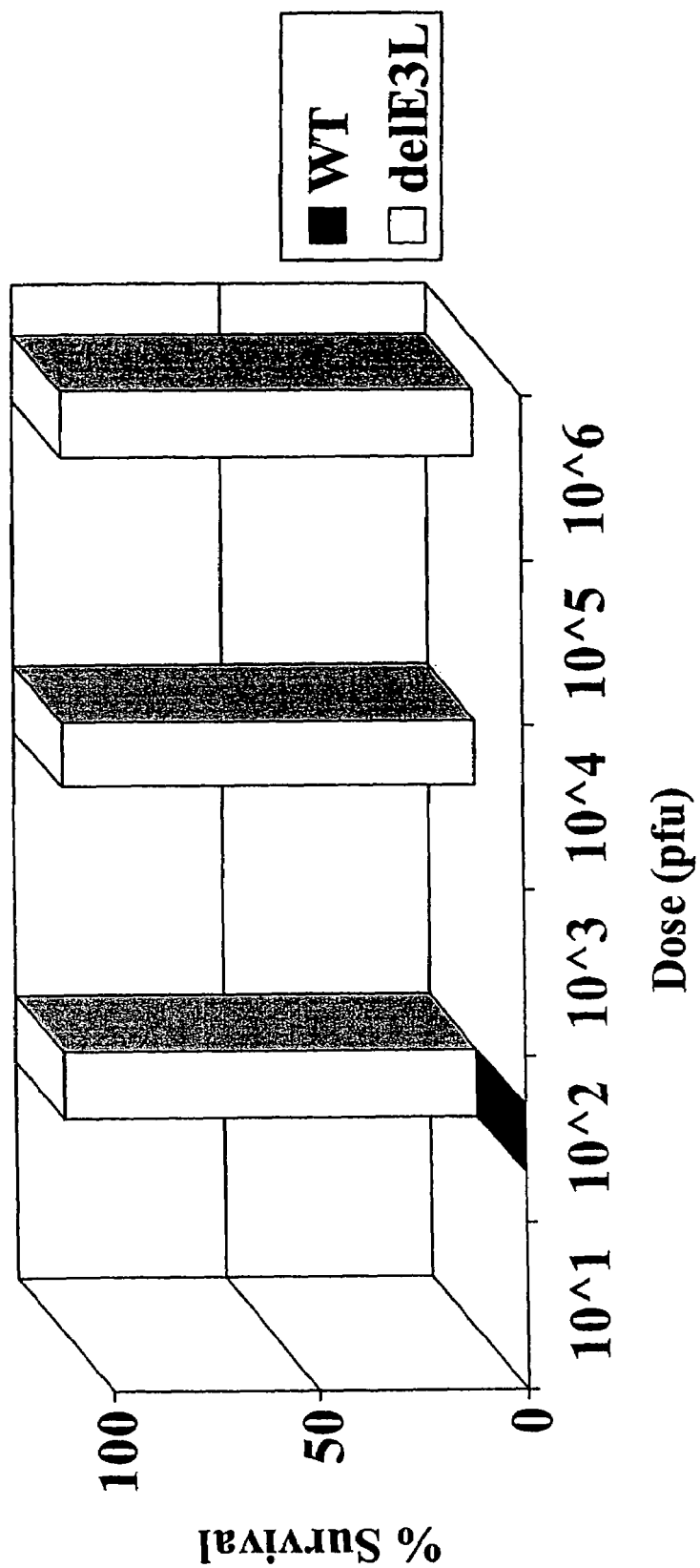
FIG. 4 is a graph depicting survival of SCID mice following intranasal injection with vaccinia virus.
Figure 5:
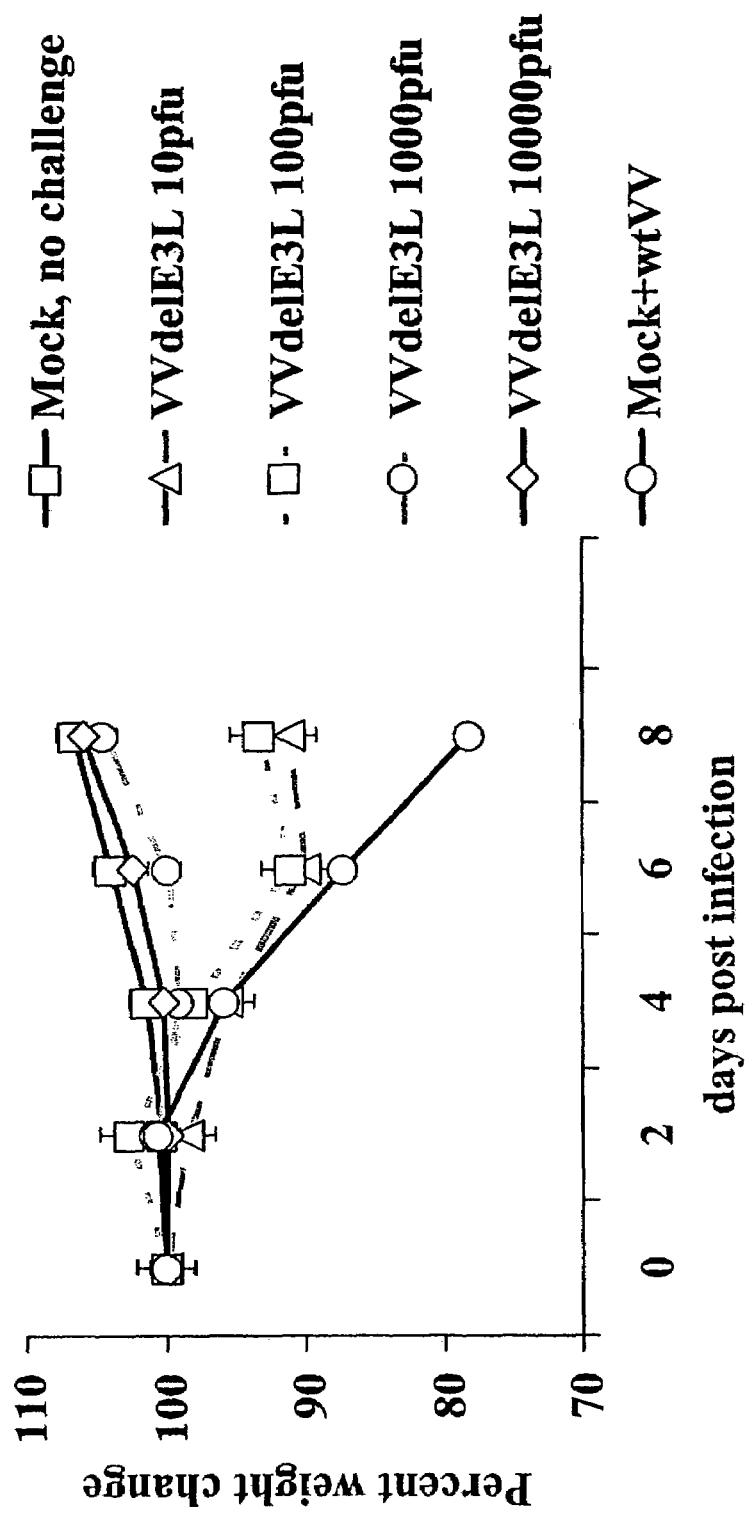
FIG. 5 is a graph depicting weight change in vaccinated and unvaccinated mice after challenge with wild-type virus. The vaccine comprised recombinant vaccinia virus wherein the E3L gene was replaced with a gene encoding β-galactosidase.
Figure 6:
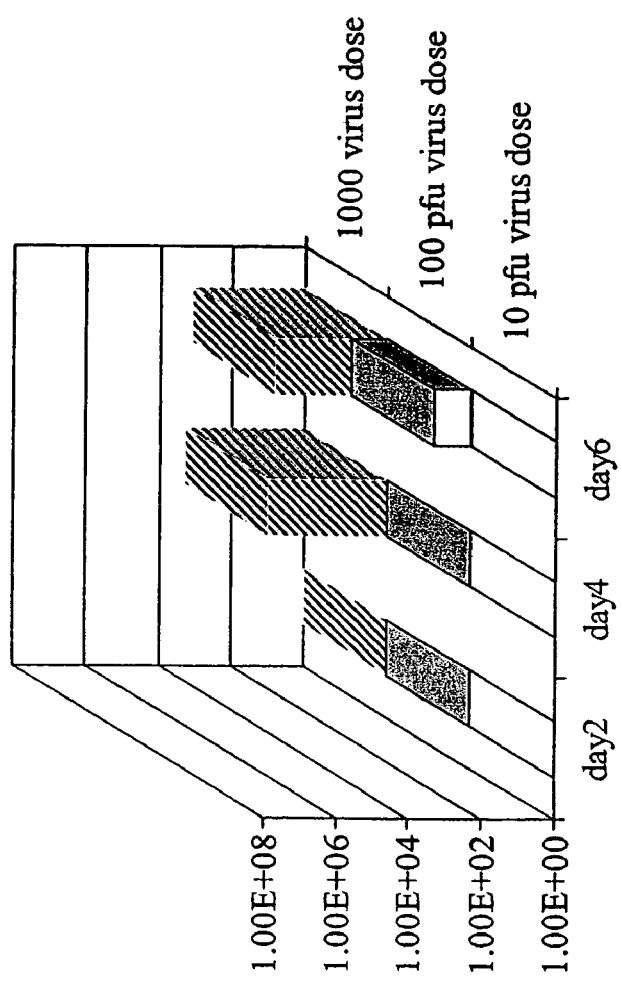
FIG. 6 is a graph depicting virus replication in the nose of infected mice.
Figure 7:
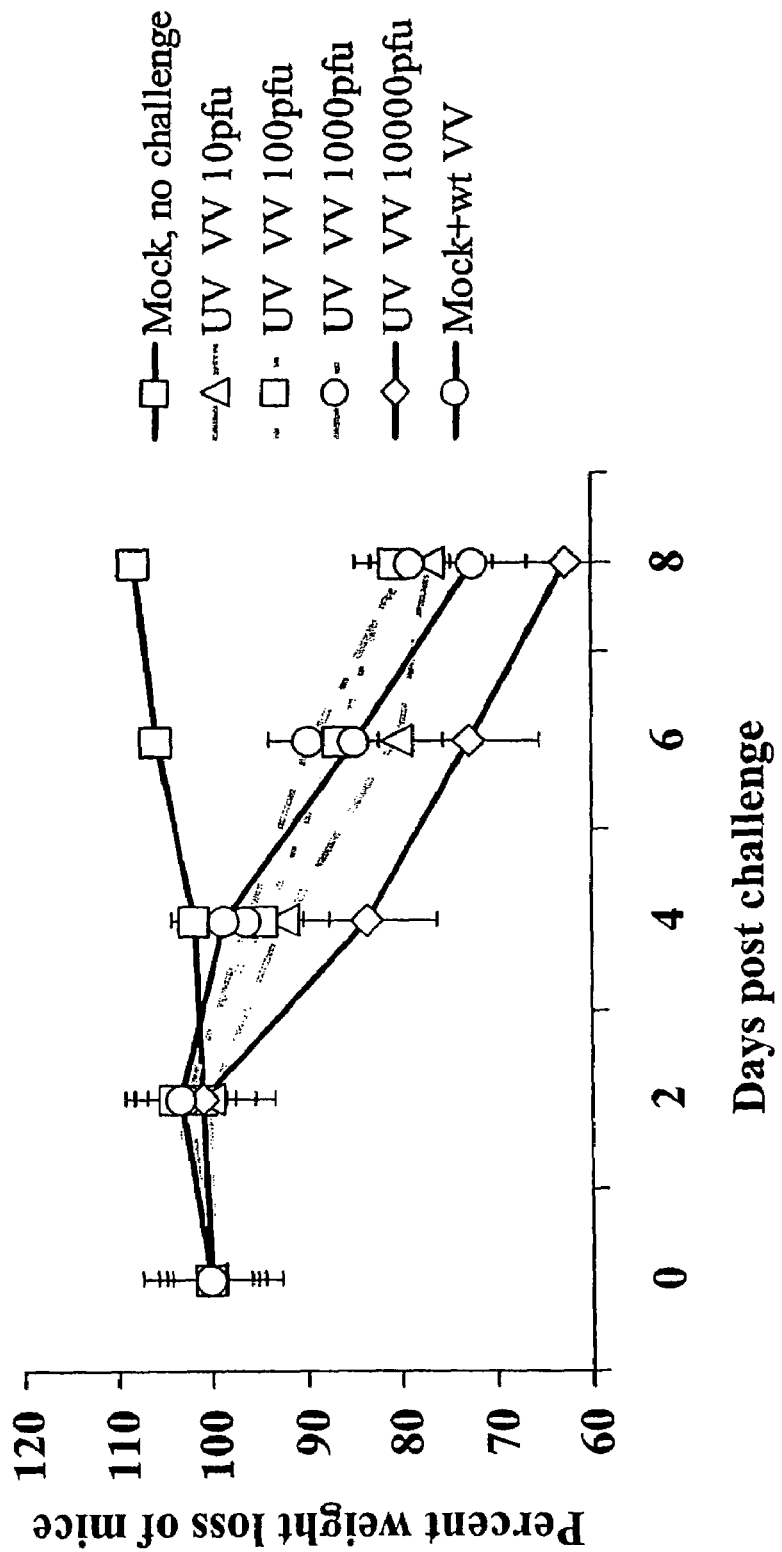
FIG. 7 is a graph depicting weight change in vaccinated and unvaccinated mice after challenge with wild-type virus. The vaccine comprised ultraviolet light-inactivated vaccinia virus.

Despite the lack of virulence and poor replication in cells in culture this virus is highly immunogenic (FIG. 4). Induction of a protective response correlated with replication of this virus in nasal mucosa (FIGS. 5 and 6). This virus could also protect against challenge with a pathogenic poxvirus when administered one day after challenge (FIG. 7). Thus, the present invention provides a viral vector that is a safe, effective vaccine for smallpox.

The present invention provides modified poxviruses in which genes that code for certain inhibitors have been substituted for the poxvirus E3L gene or that contain a modified version of the gene. These modified viruses have been found to replicate normally in cells, but display dramatically decreased pathogenesis. These viruses replicate to high titers in nasal tissues, but have a decreased propensity to spread to the lungs and brain and have decreased neurovirulence. These vectors can be used to protect against subsequent infection with vaccinia virus and, therefore, have utility in vaccination against various diseases including smallpox.

The invention further provides a safe replication-competent vector for expression of heterologous proteins. Specifically, the invention provides recombinant vaccinia viral vectors comprising the recombinant vaccinia virus described above and further containing exogenous, i.e., nonvaccinia virus, DNA. Exogenous DNA may encode any desired product, including for example, an antigen, an anticancer agent, or a marker or reporter gene product. The recombinant vaccinia virus may further have deletions or inactivations of nonessential virus-encoded gene functions. Nonessential gene functions are those which are not required for viral replication in a host cell. The exogenous DNA is preferably operably linked to regulatory elements that control expression thereof. The regulatory elements are preferably derived from vaccinia virus.

The present invention further provides a recombinant vaccinia virus, wherein the virus comprises a salamander ATV eIF2α homolog. According to some nonlimiting embodiments of the invention, this virus lacks a portion of the E3L gene. Thus, the invention provides, in some nonlimiting embodiments, a recombinant vaccinia virus in which a portion of the E3L gene is replaced with the eukaryotic initiation factor 2α gene (eIF2α) of Ambystoma tigrinum virus (ATV). These recombinant viruses may be interferon sensitive, but possess a broad host range, thus partially rescuing the phenotype of VV deleted for E3L gene. These viruses may inhibit PKR by proteolytic degradation of PKR. Infection with this virus may lead to activation of IRF-3, which is a transcription factor responsible for the induction of IFN in virus infected cells. Thus, this virus may block the activity of PKR, but cannot block the induction of IFN. Subsequent IFN sensitivity of this virus may occur through alternative IFN-induced, antiviral activity, possibly involving OAS.

According to some nonlimiting examples of the invention, replacing the E3L gene of VV with the eIF2α homolog partially restored the wild type phenotype to the recombinant virus. The E3L gene of VV provides IFN resistance, a wide host range phenotype and inhibits apoptosis (Kibler et al., 1997, *J Virol* 71(3):1992-2003; Shors et al., 1997, *Virology* 239(2):269-76). It also functions as an inhibitor of PKR (Chang et al., 1992, *Proc Natl Acad Sci USA* 89(11):4825-9; Romano et al., 1998, *Mol Cell Biol* 18(12):7304-16), OAS (Rivas et al., 1998, *Virology* 243(2):406-14) and IRF-3 phosphorylation (Smith et al., 2001, *J Biol Chem* 276(12):8951-7). Thus, recombinant viruses of the invention may resemble the wtVV in having a broad host range and in inhibiting PKR activity. At the same time recombinant viruses of the invention may also resemble VVΔE3L in being IFN sensitive and leading to OAS activity and IRF-3 translocation to the nucleus.

The recombinant vaccinia virus of the present invention may be constructed by methods known in the art, and preferably by homologous recombination. Standard homologous recombination techniques utilize transfection with DNA fragments or plasmids containing sequences homologous to viral DNA, and infection with wild-type or recombinant vaccinia virus, to achieve recombination in infected cells. Conventional marker rescue techniques may be used to identify recombinant vaccinia virus. Representative methods for production of recombinant vaccinia virus by homologous recombination are disclosed by Piccini et al., 1987, Methods in Enzymology 153:545.

For example, the recombinant vaccinia virus of a preferred embodiment of the present invention may be constructed by infecting host cells with vaccinia virus from which the E3L gene has been deleted, and transfecting the host cells with a plasmid containing a nucleic acid encoding gene product of interest flanked by sequences homologous to the left and right arms that flank the vaccinia virus E3L gene. The vaccinia virus used for preparing the recombinant vaccinia virus of the invention may be a naturally occurring or engineered strain. Strains useful as human and veterinary vaccines are particularly preferred and are well-known and commercially available. Such strains include Wyeth, Lister, WR, and engineered deletion mutants of Copenhagen such as those disclosed in U.S. Pat. No. 5,762,938. Recombination plasmids may be made by standard methods known in the art. The nucleic acid sequences of the vaccinia virus E3L gene and the left and right flanking arms are well-known in the art, and may be found for example, in Earl et al., 1993, in *Genetic Maps: locus maps of complex genomes*, O'Brien, ed., Cold Spring Harbor Laboratory Press, 1.157 and Goebel et al., 1990, supra. The amino acid numbering used herein is adopted from Goebel et al., 1990, supra. The vaccinia virus used for recombination may contain other deletions, inactivations, or exogenous DNA as described hereinabove.

Following infection and transfection, recombinants can be identified by selection for the presence or absence of markers on the vaccinia virus and plasmid. Recombinant vaccinia virus may be extracted from the host cells by standard methods, for example by rounds of freezing and thawing.

The resulting recombinant vaccinia virus may be further modified by homologous recombination to provide other deletions, inactivations, or to insert exogenous DNA.

The recombinant vaccinia viruses and compositions of the present invention may be used as expression vectors in vitro for the production of recombinant gene products, or as delivery systems for gene products, as human or veterinary vaccines, or anticancer agents. Such utilities for recombinant vaccinia viruses are known in the art, and disclosed for example by Moss, 1996, "Poxviridae: The Viruses and Their Replication" in *Virology*, Fields et al., eds., Lippincott-Raven, Philadelphia, pp. 2637-2671.

The present invention further provides a method of making a recombinant gene product comprising subjecting a recombinant vaccinia viral vector having a deletion of the E3L gene and further comprising exogenous DNA that encodes the recombinant gene product operably linked to the control of regulatory elements that control expression thereof, to conditions whereby said recombinant gene product is expressed, and optionally recovering the recombinant gene product. In a preferred embodiment, the recombinant gene product is an antigen that induces an antigenic and/or immunogenic response when the gene product or a vector that expresses it is administered to a mammal.

The present invention further provides vaccines for providing immunological protection against vaccinia virus, or heterologously expressed polypeptides, wherein said vaccines comprise a recombinant vaccinia viral vector and a carrier. The term carrier as used herein includes any and all solvents, diluents, dispersion media, antibacterial and antifungal agents, microcapsules, liposomes, cationic lipid carriers, isotonic and absorption delaying agents, and the like. Suitable carriers are known to those of skill in the art. The vaccine compositions of the invention can be prepared in liquid forms, lyophilized forms or aerosolized forms. Other optional components, e.g., stabilizers, buffers, preservatives, flavorings, excipients and the like, can be added. In addition, adjuvants may be used to boost or augment immune responses. Optionally, the vaccine may be formulated to contain other active ingredients and/or immunizing antigens.

Also included in the invention is a method of vaccinating a host, including but not limited to mammals such as a humans, against vaccinia virus infection or heterologously expressed proteins with the novel vaccine compositions of the invention. The vaccine compositions, including one or more of the recombinant vaccinia viruses described herein, are administered using routes typically used for immunization, i.e., subcutaneous, oral, or nasal administration, in a suitable dose. The dosage regimen involved in the method for vaccination, including the timing, number and amounts of booster vaccines, will be determined considering various hosts and environmental factors, e.g., the age of the patients, time of administration and the geographical location and environment.

All documents cited throughout this specification are incorporated herein in their entirety by reference.

EXAMPLES

This invention will be better understood from the following examples. However, one skilled in the art will readily appreciate the specific materials and results described are merely illustrative of, and are not intended to, nor should be intended to, limit the invention as described more fully in the claims which follows thereafter.

Example 1

Construction of Recombinant Vaccinia Virus

The β-galactosidase gene under the control of the vaccinia virus 11 k promoter was cloned into PMPE3delGPT plasmid. This plasmid was used for in vivo recombination with the WR strain of vaccinia virus. Recombinants were isolated by three rounds of plaque purification on a monolayer of BHK-13 cells stained with X-Gal. Deletion of the E3L gene was confirmed by western blotting with E3L specific antibody. PMPE3LdelGPT plasmid, the process of in vivo recombination and isolation of recombinants have been previously described in Kibler et al. (1997, *J Virol* 71(3):1992-2003).

Example 2

Survival of Mice Following Intranasal Infection with Vaccinia Virus

Figure 1:
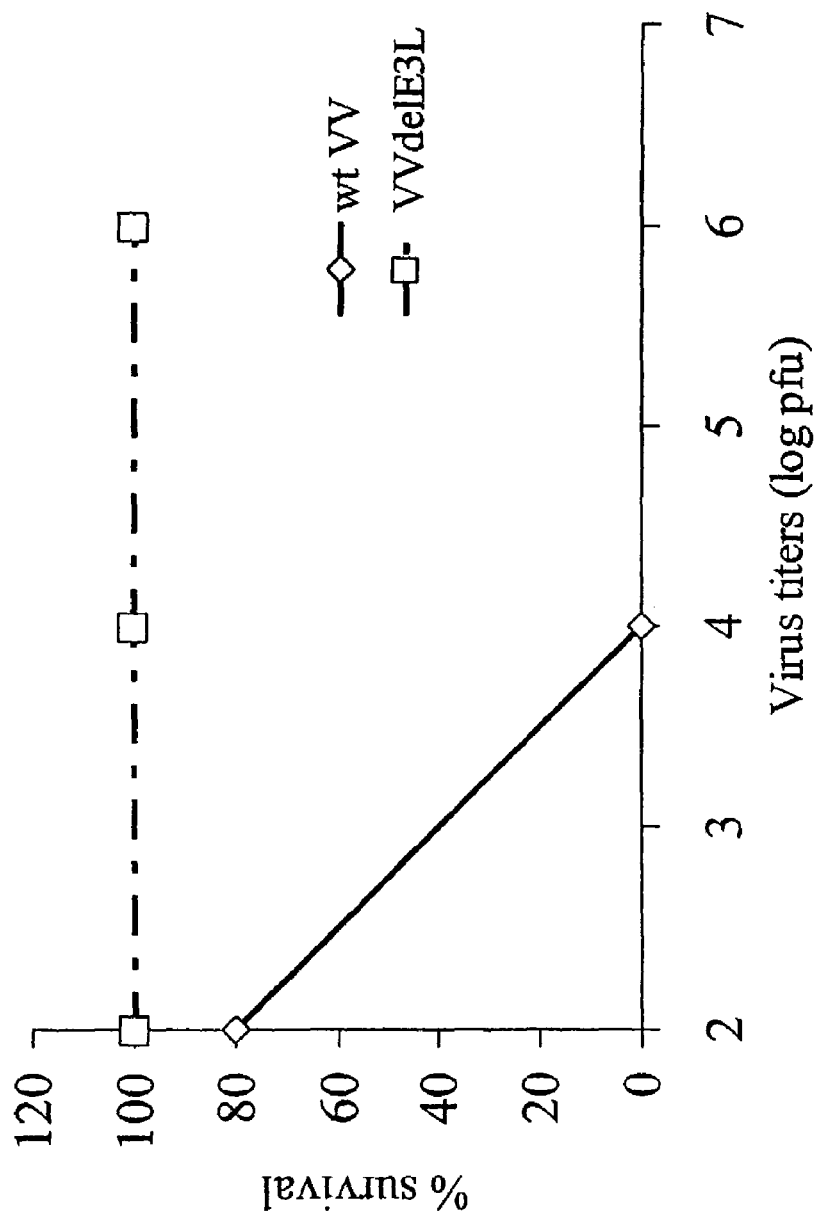
FIG. 1 is a graph depicting survival of mice following intranasal injection with vaccinia virus.

Groups of 5 C57BL/6 mice were infected with different doses of wild type (wt) vaccinia virus (VV) and VV deleted for the E3L gene (VVΔE3L), by intranasal route. There was 100% survival of mice infected with the highest dose ($10^6$) of the mutant virus while wtVV had an $LD_{50}$ or approximately $10^3$ pfu. The mutant VV construct was over 1000-fold less pathogenic than wtVV (FIG. 1).

Example 3

Tissue Distribution of Virus

Figure 2:
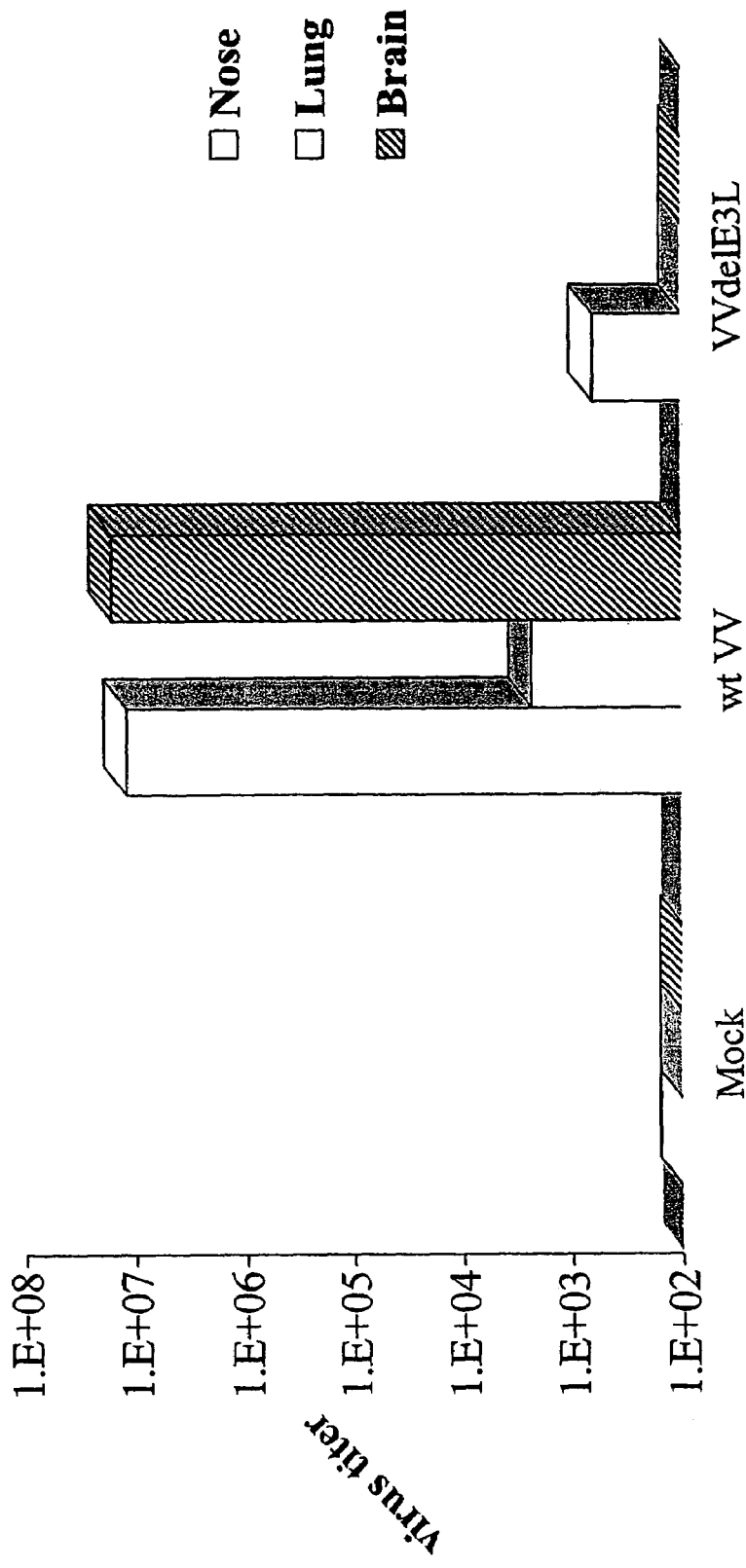
FIG. 2 is a graph depicting tissue distribution of vaccinia virus after intranasal injection.

Groups of 3 C57BL/6 mice were infected with $10^6$ plaque-forming units of wtVV and VVΔE3L by intranasal route. Tissues were harvested, processed and titrated in RK-13 cell line. The figure represents the average titer per gram of tissue of the 3 mice infected with each virus. Wild type VV was detected in the nasal turbinates, lungs, and brain by 5 days post infection. VVΔE3L was detected in the nasal turbinates, but they did not spread to the lung and brain. 4 of the 5 VV mutants replicated to high titers in the nose following infection (FIG. 2).

Example 4

Intracranial Infection of Mice with wtVV and VVΔE3L

Figure 3:
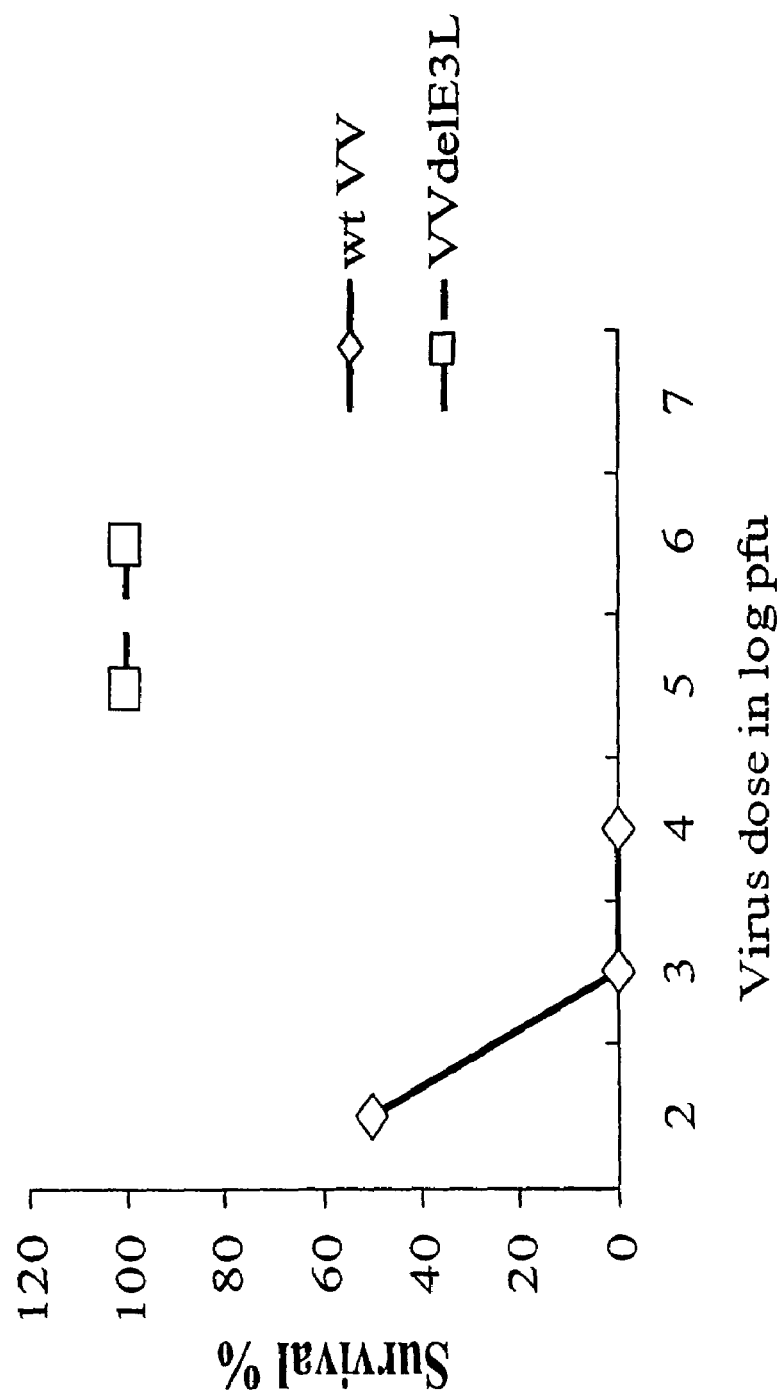
FIG. 3 is a graph depicting survival of mice following intracranial injection with various recombinant vaccinia viruses.

Groups of 5 C57BL/6 mice were infected with different doses of wtVV and VVΔE3L by intracranial injection. The infected mice were observed for 2 weeks following infection and all mortalities were recorded. VVΔE3L was greater than 4 logs less neurovirulent than wtVV (FIG. 3).

Example 5

Intranasal Infection of SCID Mice with wtVV and VVΔE3L

Groups of 5 SCID mice were infected intranasally with different doses of wtVV or with VVΔE3L. The $LD_{50}$ for wtVV was less than 100 pfu. VVΔE3L did not kill mice, even at the highest dose administered (FIG. 4).

Example 6

Resistance of VVΔE3L-Vaccinated Mice

Groups of 5 C57BL/6 mice were immunized with different doses (ranging from 10 to 10,000 pfu) of recombinant vaccinia virus expressing the β-galactosidase gene in place of VV E3L. One month later the immunized mice and the unimmunized controls (mock) were challenged with $10^6$ pfu of wtVV. The results depicted in FIG. 5 are the average of 2 independent experiments. Error bars represent standard error. Weight loss was used as an indicator of disease due to wtVV. Severe weight loss was observed in the unimmunized control. Weight loss of mice vaccinated with 10 pfu (p=0.09) and 100 pfu (p=0.081) of VVΔE3L was not significantly different from mock vaccinated mice challenged with wtVV, but 1000 pfu (p<0.001) was significantly different at an α of 0.05. Therefore, vaccination with 1000 pfu and above of VVΔE3L was sufficient to protect against VV challenge.

Example 7

Virus Replication in the Nose of Infected Mice

Low doses of VVΔE3L (10, 100, and 1000 pfu) were administered by intranasal route to C57BL/6 mice. The noses of 3 mice infected with each dose of each virus were harvested on post-infection days 2, 4, and 6. The harvested tissues were processed and titrated in RK-13 cell line. The average viral load in the nose of mice infected on each of those days is shown in FIG. 6.

Example 8

Resistance of Mice Vaccinated with UV-Inactivated Virus

Groups of 5 C57BL/6 mice were immunized with different doses (ranging from 10 to 10,000 pfu) of UV-inactivated VV. One month later the immunized mice and the unimmunized controls (mock+wtVV) were challenged with $10^6$ pfu of wtVV. Weight loss was used as an indicator of disease due to wtVV. Severe weight loss was recorded in all the mice vaccinated with the UV-inactivated virus (FIG. 7). Error bars represent standard error.

Example 9

Resistance of VVΔE3L-Vaccinated Mice

Figure 8:
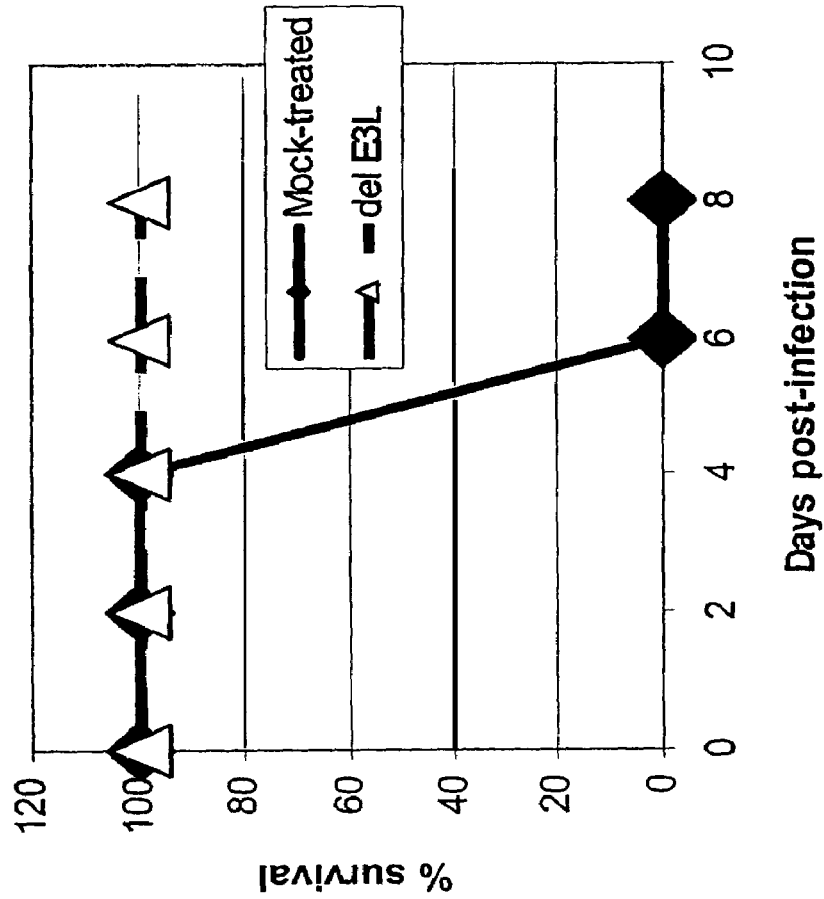
FIG. 8 is a graph depicting the survival of mice following intranasal injection with vaccinia virus.

Groups of 5 C57BL/6 mice were infected intranasally with $10^4$ pfu of wtVV (approximately 1 $LD_{50}$). One day later animals were immunized with $10^6$ pfu of VVΔE3L. All unimmunized animals died, while animals immunized post-exposure with VVΔE3L survived (FIG. 8).

Example 10

Interferon Sensitivity Assay

RK-13 cells were set down at 50% confluency in 6 well plates. Four hours later the media overlaying the cells were replaced with media containing different doses of rabbit interferon (480 U/μl, Lee Biomolecular) so that the final concentration of IFN ranged from 0 U/ml to 1000 U/ml of cell culture media. Sixteen hours following IFN treatment these cells were infected with 100 pfu of each virus. Wt VV was used as a positive control since it is resistant to the effects of IFN. VVdelE3L was used as a negative control. The infected cells were incubated at 37° C. and 5% $CO_2$ for 36-48 hours following which they were stained with 0.1% crystal violet in 20% ethanol for 1 minute at room temperature. The plaques were counted in each well and plaque reduction with increasing doses of IFN was computed as a percentage.

VVΔE3L was sensitive to IFN and unable to plaque in RK-13 cells pretreated with 100 and 1000 U/ml of rabbit IFNβ. This virus was also unable to plaque in HeLa cells even in the absence of IFN treatment (Beattie E et al., 1996, *Virus Genes* 12(1), 89-94).

Example 11

Cell Lines

Rabbit kidney (RK-13) cells were maintained in Eagle's Minimal Essential Medium (Gibco BRL) supplemented with 5% fetal bovine serum (Irvine Scientific), 50 μg/ml gentamycin sulfate and 0.1 mM non-essential amino acids and vitamins (Gibco BRL). Baby Hamster Kidney (BHK-21) cells were maintained in the same media containing the same amount of non-essential amino acids, vitamins and gentamycin but supplemented with 10% fetal bovine serum. HeLa cells (S3 HeLa cells from ATCC and S3 HeLa cells generously provided by Frederick) were grown in Dulbecco's Modified-Minimal Essential Medium (DMEM) (Gibco BRL) containing 5% fetal bovine serum and 50 µg/ml gentamycin sulfate. Unless otherwise notified, HeLa cells used in this study were S3 HeLa cells from Frederick. All cells were incubated at 37° C. in the presence of 5% $CO_2$.

Example 12

Plasmids

The eIF2α homolog gene from *Ambystoma tigrinum* virus (ATV) kindly provided by James Jancovich, was recombined into the E3L locus of vaccinia virus (VV) deleted for E3L (VVΔE3L), using the plasmid pMPE3LΔgptMCS (previously described by Kibler et al., 1997, *J Virol* 71(3):1992-2003). The eIF2α homolog gene was attained by PCR from the plasmid pSTBlue-1 (clone was kindly provided by James Jancovich), with primers containing a BamHI site at the 5' end and a SalI at the 3' end of the gene (5' ATT AGG ATC CGC CAT GGC ACA CAA CAG GTT TTA CAG 3', SEQ ID NO:4; 5' ATT AGT CGA CAT ATC ACA CAA AGG GGC ACA GTC C 3', SEQ ID NO:5). The PCR products were gel extracted (Qiagen), purified and digested with BamHI and SalI, and ligated into pMPE3LΔgptMCS digested with the same enzymes. Colonies were screened by restriction digests with BamHI and SalI and also by sequencing. Thus this ligation resulted in the formation of pMPE3LΔgptMCS-ATV eIF2α.

Example 13

Transfection and In Vivo Recombination

In vivo recombination (IVR) was performed as described by Kibler et al. (1997, *J Virol* 71(3):1992-2003). The recombination vector pMPE3LΔgptMCS has the *E. coli* gpt gene as a selectable marker and regions homologous to the flanking arms of the E3L gene in VV on either side of the multiple cloning site to facilitate recombination into the E3L locus. Ecogpt is the *E. coli* guanosine phosphoribosyl transferase gene. This gene allows conversion of xanthine to guanine monophosphate (GMP), without needing the intermediate steps of converting inosine monophosphate (IMP) to xanthine monophosphate (XMP), ultimately resulting in GMP. This is useful in selecting recombinants in the presence of mycophenolic acid (MPA), which is responsible for inhibiting eukaryotic production of GMP, by blocking the conversion of IMP to XMP. Adding xanthine and MPA to the ecogpt selection media, pressure can be applied to select for recombinants containing the pMPE3LΔgptMCS plasmid with the desired insert. In the presence of MPA only the viruses expressing the gpt gene are able to grow thus enabling selection of recombinants.

VVΔE3L, the virus used for recombining this gene into the E3L locus of VV, has a LacZ gene in place of E3L thus allowing for blue white selection of the recombinant virus using X-gal substrate at a final concentration of 200 µg/ml. Subconfluent BHK cells were used for both transfection and in vivo recombination. Cells were set down in 35 mm dishes and were pretreated for 30 minutes with 2 ml of Opti-MEM (Gibco BRL) at 37° C. The cells were transfected with 1 µg of plasmid DNA using LipofectACE (Gibco BRL) as per manufacturer's instructions. The cells were simultaneously infected with VVΔE3L at a multiplicity of infection (moi) of 0.05, allowed to incubate for 1 hour, with rocking at 37° C., 5% $CO_2$ and overlaid with Opti-MEM containing 1% FBS. At 36 hours post infection, the cells were harvested, pelleted by centrifugation at 1000 rpm, 4° C. for 10 minutes and resuspended in 200 µl of 1 mM Tris HCl pH 8.8. Cells were then subjected to three rounds of freezing and thawing in order to release the virus from the cells.

Example 14

MPA Selection of Recombinants

The resultant recombinant virus from above was used to infect 60 mm dishes of confluent BHK cells which had been pretreated for 6 hours prior to infection with ecogpt selection media (complete BHK media containing 10% FBS, 10 µg/ml MPA, 250 µg/ml xanthine and 15 µg/ml hypoxanthine). The infection was carried out for 1 hour and then overlaid with 5 ml of ecogpt selection media. 48-72 hours post infection, the liquid overlay media was replaced with 1.5% agarose supplemented with complete 2×MEM media, 10 µg/ml MPA, 250 µg/ml xanthine, 15 µg/ml hypoxanthine and 200 µg/ml X-gal (Gold Biotechnology, Inc.). 6 hours later blue plaques were picked into 200 µl of 1 mM Tris HCl pH 8.8 and three rounds of freeze thaws were completed. This whole process was repeated three times in order to pick a purified blue plaque. After this selection, the removal of the ecogpt media causes a second recombination event to occur. By removing the MPA selective pressure, VVΔE3L either removes the lacZ gene in place of the E3L gene, keeping the ATV eIF2α homolog gene or, it can remove the ATV eIF2α homolog gene and retain the original lacZ in place. Virus that has retained the lacZ gene will appear as blue plaques in the presence of X-gal, and viral plaques that have retained the ATV eIF2α homolog gene will be clear or colorless. The fourth round of plaquing was done in RK-13 cells in the absence of ecogpt selection media and when plaques were visible the cells were overlaid with 1.5% agarose, complete 2×MEM media and 0.2 mg/ml X-gal. Both clear and blue plaques were visible. 6 hours later the clear plaques were picked in 200 µl of 1 mM Tris HCl pH 8.8 and plaque purified for two more rounds when only clear plaques were visible.

Example 15

Amplification of Virus

In order to make a working stock of virus, purified plaques must be amplified. BHK cells were set down in five 100 mm dishes with a confluency of 100%. Each dish was infected with a mixture of 40 µl of the viral plaque resuspended in 160 µl of 1×MEM, 2% FBS and 50 µg/ml gentamycin sulfate. After one hour of infection at 37° C., 5% $CO_2$ cells were overlaid with complete BHK media. The infection was allowed to proceed to 100% cytopathic effect (CPE). Cells were then harvested and pelleted by centrifugation at 1000 rpm, 4° C., for 10 minutes. The supernatant was removed and the pellet was resuspended in 1 ml of 1×MEM containing 2% FBS and 50 µg/ml gentamycin sulfate. Three rounds of freeze thaws were done to release the virus from the cells and the cells were centrifuged at 1000 rpm, 4° C., for 10 minutes to spin down the cell debris. Aliquots of 200 µl of the supernatant were transferred into cryogenic tubes and stored at −80° C.

Example 16

Calculating the Titer of the Virus

RK-13 cells were used to calculate the titer of the virus in plaque-forming units per ml (pfu/ml). Cells were set down at 100% in 6 well plates and infected with serial dilutions of the amplified virus. The dilutions ranged from $10^{-3}$ to $10^{-8}$ and each well of the plate was infected with 100 µl of each dilution. The infection was allowed to proceed until the plaques were visible. Cells were then stained with 0.1% crystal violet in 20% ethanol. The number of plaques were counted in a well that has 30-300 plaques and the titer was determined by multiplying the number of plaques with the dilution factor.

Example 17

Sequencing Viruses

100 µl of ATV virus stock of $10^8$ pfu/ml titer was used to extract DNA for viral PCR. To the 100 µl of virus stock, 100 µl of phenol was added and centrifuged at 10000 rpm for 5 minutes at 4° C. The aqueous layer from this step was re-extracted with 50 µl phenol and 50 µl chloroform isoamyl alcohol (24:1) and centrifuged as above. The aqueous layer from this step was again extracted with 100 µl chloroform isoamyl alcohol (24:1) and precipitated with 2.5 volumes of 100% ethanol and 1/10 volume of 3 M sodium acetate, pH 5.2. The DNA was rinsed twice with 70% ethanol, dried and resuspended in 10 µl glass distilled water.

The ATV eIF2α, gene was amplified from this viral DNA by PCR using primers that anneal to the flanking regions of the E3L gene (5' CGAACCACCAGAGGATG 3' (SEQ ID NO:6) and 5' TAGTCGCGTTAATAGTACTAC 3' (SEQ ID NO:7)). The amplified product was run on 0.8% GTG agarose (FMC Bioproducts) gel and the band was cut out. The DNA was extracted from the band of interest by first freezing the band overnight at −80° C. and then thawing it at 37° C. for 30 minutes. The supernatant was separated by centrifugation at 4° C. for 15 minutes at 10,000 g and subjected to ethanol precipitation. The DNA was resuspended in 10 µl of glass distilled water. 1 µl of each of the primers (10 µM stock) used for PCR was added to 5 µl of DNA and sequenced by Dideoxy method.

Example 18

Recombinant Vaccinia Virus Construction

The eIF2α homolog from ATV has sequence homology to the eukaryotic translation initiation factor, eIF2α and also to the K3L of vaccinia virus (FIG. 9). To examine it's ability to inhibit PKR activity, eIF2α homolog was inserted into the E3L locus of VV (VVΔE3L/ATV eIF2α) utilizing in vivo recombination as described in Example 13. In order to confirm if the eIF2α homolog was inserted into the E3L locus, viral DNA was extracted and amplified by PCR using E3L flanking primers. A product of correct size (780 bp) was obtained indicating that eIF2α homolog is in the E3L locus of VV. To further confirm that the eIF2α homolog gene has been correctly recombined into the E3L locus, the band of the amplified product was cut out from the gel, gel extracted, purified and the DNA was sequenced by dideoxy method.

Example 19

Interferon Sensitivity Assay

RK-13 cells were seeded at 50% confluency in 6 well plates. 4 hours later the wells were treated with 0, 1, 10, 100 and 1000 U/ml of rabbit interferon (Lee Biomolecular). 16 hours post interferon treatment, cells were infected with 200 pfu of wtVV, VVΔE3L, and VVΔE3L/ATV eIF2α virus. Wild type vaccinia virus (wtVV) was used as a positive control as it is resistant to the effects of IFN and VVΔE3L was used as a negative control as it is sensitive to IFN. The infected cells were incubated at 37° C., 5% $CO_2$ for 24 hours. Then they were stained with 0.1% crystal violet in 20% ethanol. The plaques were counted in each well and plaque reduction with increasing doses of IFN was computed as a percentage.

Figure 10:
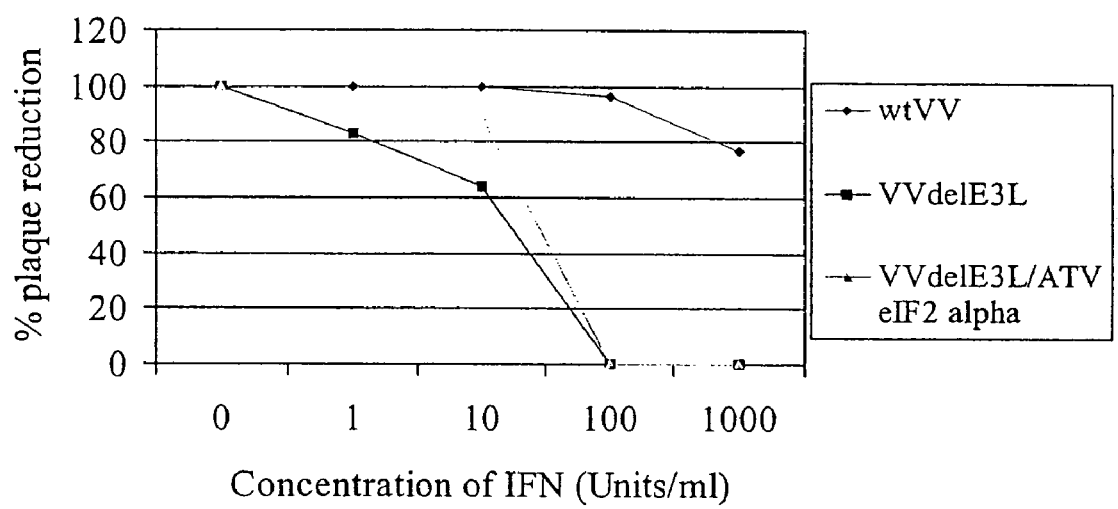
FIG. 10. Interferon sensitivity assay. Six well plates of RK-13 cells were treated with 0, 1, 10, 100 and 1000 units/ml of rabbit interferon 16 hours prior to infection. Each well was infected with 200 pfu of wtVV, VVdelE3L or VVdelE3L/ATV eIF2α and stained with 0.1% crystal violet in 20% ethanol 24 hours post infection. The number of plaques formed in the presence of the various amounts of interferon were counted and compared to the number of plaques formed in the absence of interferon to determine the percentage of plaque reduction in the presence of interferon.
Figure 11:
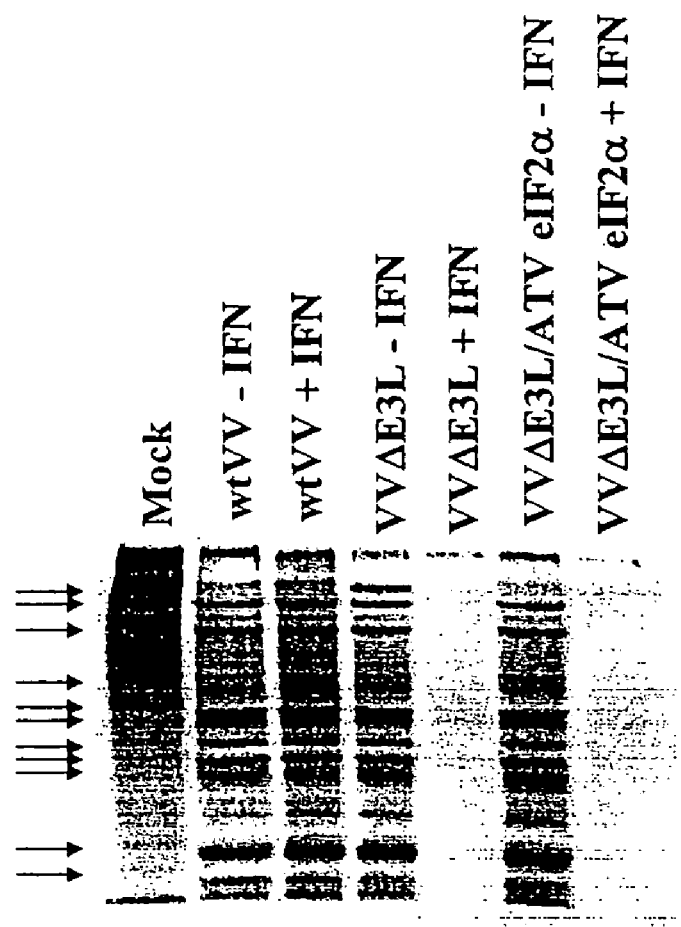
FIG. 11. [$^{35}$S] methionine labeling at 6 hpi in RK-13 cells. RK-13 cells were infected at a moi of 5 in the presence or absence of 100 units/ml of rabbit interferon. Cells were starved for methionine by incubating them in media lacking methionine for 30 minutes. Cells were then labeled using media containing 50 μCi/ml of [$^{35}$S] methionine for one hour. Cells were harvested as described in materials and methods and the proteins were separated on 12% SDS-PAGE gel, stained and exposed to X-ray film. The arrows indicate viral proteins.
Figure 12:
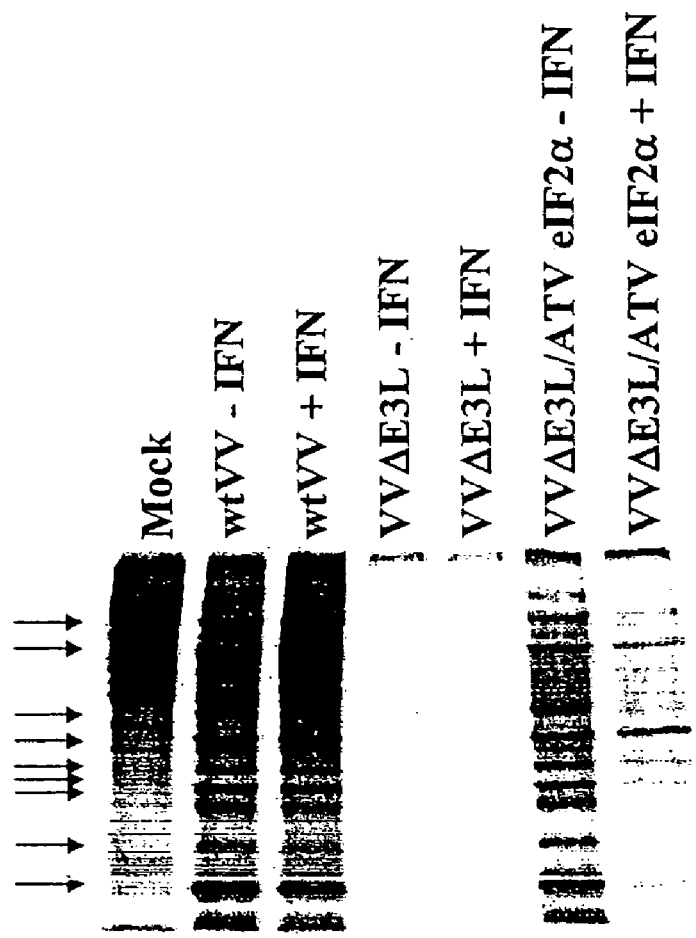
FIG. 12. [$^{35}$S] methionine labeling a 6 hpi in HeLa cells. HeLa cells were infected at a moi of 5 in the presence or absence of 100 units/ml of human interferon. Cells were starved for methionine by incubating them in media lacking methionine for 30 minutes. Cells were then labeled using media containing 50 μCi/ml of [$^{35}$S] methionine for one hour. Cells were harvested as described in materials and methods and the proteins were separated on 12% SDS-PAGE gel, stained and exposed to X-ray film. The arrows indicate viral proteins.
Figure 13:
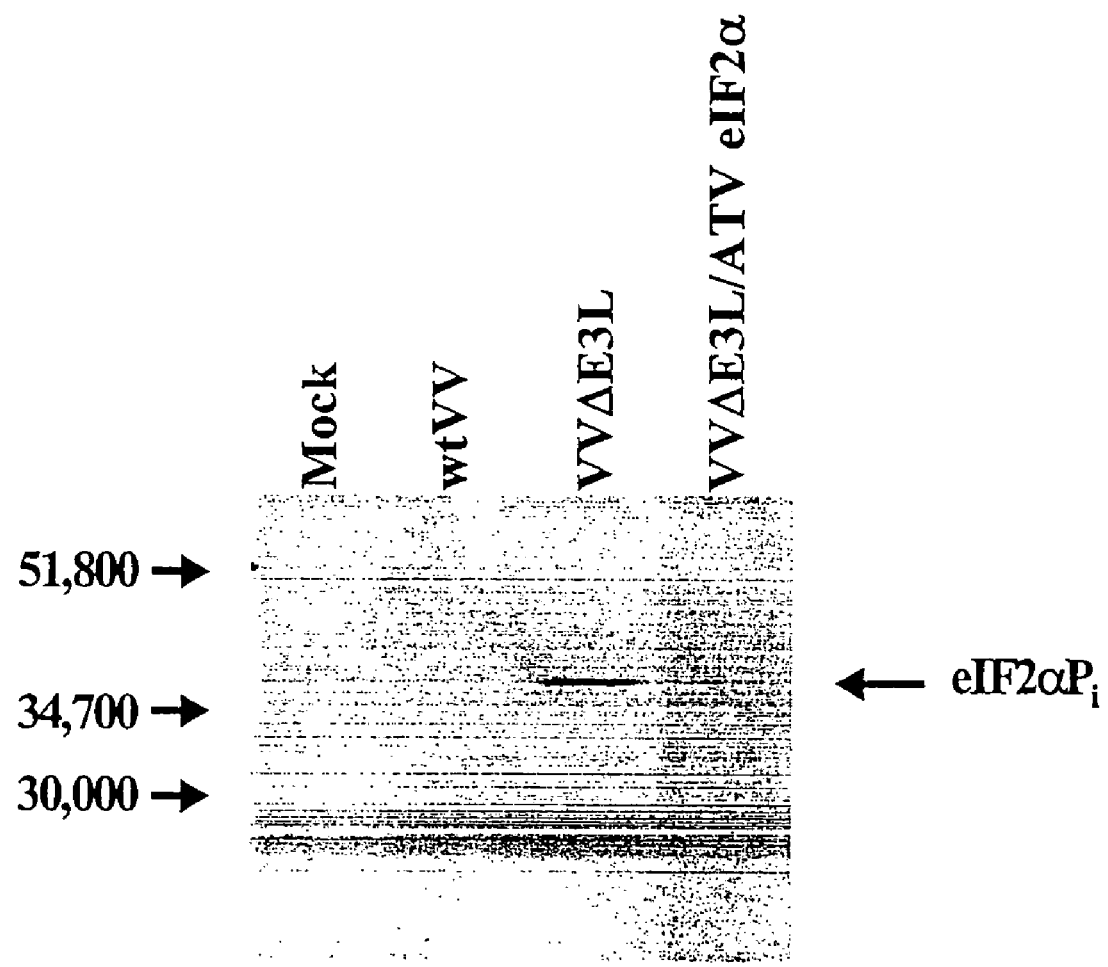
FIG. 13. eIF2α phosphorylation. HeLa cells were mock infected or infected with wtVV, VVΔE3L, or VVΔE3L/ATV eIF2α at a moi of 5 and harvested at 6 hpi. Whole cell extracts were prepared as described in materials and methods. Extracts were run on SDS-PAGE gel, transferred to nitrocellulose, and assayed by chemiluminiscent western blot. Antibodies to phosphorylated eIF2α were used to detect the presence of phosphorylated eIF2α.

Wild type vaccinia virus (wtVV) is resistant to the antiviral effects of IFN and plaques in RK-13 cells pretreated with rabbit interferon up to 1000 units/ml. It has been shown that the N-terminal domain of E3L is necessary and sufficient for IFN resistance (Kibler et al., 1997, *J Virol* 71(3):1992-2003; Shors et al., 1997, *Virology* 239(2):269-76). VVΔE3L is IFN sensitive (Shors et al., 1997, *Virology* 239(2):269-76) and is totally unable to replicate in the presence of 100 units/ml in RK-13 cells. To determine if the eIF2α homolog can provide IFN resistance to VVΔE3L, 6 well plates of confluent RK-13 cells were pretreated with 0, 1, 10, 100 and 1000 units/ml of rabbit IFN. Each well was infected with 200 pfu of wtVV, VVΔE3L, VVΔE3L/ATV eIF2α, and stained with crystal violet once plaques were visible. The number of plaques were counted and recorded in Table 1. FIG. 10 shows the results of the IFN sensitivity assay. It is evident from the figure that wtVV is IFN resistant and grows even in the presence of 1000 units/ml of IFN and VVΔE3L is IFN sensitive and is not able to grow in 100 units/ml of IFN. The recombinant virus, VVΔE3L/ATV eIF2α is also IFN sensitive and doesn't grow in the presence of 100 units/ml of IFN.

TABLE 1

PLAQUING EFFICIENCY IN DIFFERENT CELL LINES

| | Cells | | | | | |
| --- | --- | --- | --- | --- | --- | --- |
| | HeLa | RK-13 0U IFN/ml | RK-13 1U IFN/ml | RK-13 10U IFN/ml | RK-13 100U IFN/ml | RK13 1000U IFN/ml |
| wtVV | 178 | 303 | 303 | 302 | 291 | 233 |
| VVΔE3L | 0 | 211 | 175 | 135 | 0 | 0 |
| VVΔE3L/ATV eIF2α | 0 | 140 | 130 | 125 | 0 | 0 |

Note. HeLa cells and RK-13 cells (+/−IFN) were infected with 200 Pfu's of wt VV, VVΔE3L, VVΔE3L/ATV eIF2α and 24 hours post infection plates were stained with 0.1% crystal violet in 20% ethanol and the number of plaques were counted and shown in the table above.

Example 20

Host Range wtVV has a broad host range and is able to form plaques in HeLa cells while VVΔE3L is unable to replicate in HeLa cells, and therefore has a limited host range. The ability of the recombinant virus (VVΔE3L/ATV eIF2α) to plaque in HeLa and RK-13 cells was determined by infecting 6 well plates of these cell lines at 90% confluency. Cells were infected with serial dilutions of each of the viruses. In some assays, cells were infected with 200 pfu of the virus. wtVV and VVΔE3L were used as positive and negative controls respectively. Infection was continued until the formation of visible plaques, following which cells were stained with 0.1% crystal violet in 20% ethanol and the plaques were counted.

The recombinant virus was able to form plaques in RK-13 cells but unable to plaque in HeLa cells. The plaquing efficiency in HeLa cells is shown in Table 1. Despite this, it has a broad host range as it replicates like wtVV in HeLa cells and is described in the next section.

Example 21

[$^{35}$S] Methionine Labeling

The activation of the two IFN-induced enzymes, PKR and OAS, leads to shutoff of protein synthesis in the infected cell. Activated PKR phosphorylates the α subunit of translation initiation factor, eIF2, thus effectively blocking protein synthesis (Levin and London, 1978, *Proc Natl Acad Sci USA* 75:1121-25; Samuel, 1979, *Proc Natl Acad Sci USA* 76(2): 600-4). To confirm the IFN sensitivity in RK-13 cells and inability to plaque in HeLa cells of the recombinant virus (VVΔE3L/ATV eIF2α), in vivo labeling assays, using [$^{35}$S] methionine, were performed in RK-13 cells and HeLa cells in the presence and absence of 100 units/ml of IFN.

60 mm dishes containing confluent monolayers of RK-13 cells in the presence or absence of 100 U/ml of rabbit interferon and HeLa cells in the presence or absence of 100 U/ml of human α A/D interferon were mock infected or infected with wtVV, VVΔE3L and VVΔE3L/ATV eIF2α at a moi of 5. The infected cells were allowed to incubate for 5 hours and 30 minutes. Cells were washed twice with 1×PBS and incubated for 30 minutes (at 37° C., 5% $CO_2$) in 2 ml labeling media (methionine-free, serum-free MEM (Sigma)) to starve the cells of methionine. Then the starvation media was removed, cells were washed twice with 1×PBS and incubated in labeling media containing 50 μCi/ml [$^{35}$S] methionine (Dupont NEN) for another one hour. Labeling media was removed and the cells were scraped into 1×PBS. The cells were pelleted by centrifugation and lysed in 100 μl of NP40 lysis buffer (20 mM HEPES, pH 7.5, 120 mM KCl, 5 mM $MgCl_2$, 1 mM DTT, 10% glycerol and 0.5% NP40). The cells were incubated on ice for 10 minutes and pelleted by centrifugation. The supernatant was stored at −80° C. and run onto a 12% SDS-PAGE gel. The gel was stained in Coomassie blue, destained, dried and exposed to X-ray film for 24-48 hours.

A shutoff of translation in VVΔE3L in RK-13 cells treated with IFN and in HeLa cells, at 6 hours post infection (hpi), but not in mock infected cells or cells infected with wtVV can be seen from FIGS. 11 and 12, respectively. The recombinant virus (VVΔE3L/ATV eIF2α) shows a shut-off of protein translation similar to VVΔE3L at 6 hpi in RK-13 cells in the presence of IFN (FIG. 11, lanes 6 and 8) but no shut-off of protein translation similar to wtVV at 6 hpi in HeLa cells in the absence of IFN (FIG. 12, lanes 3 and 7). Thus it is clear that the recombinant virus can replicate normally in HeLa cells but is not able to form plaques.

Example 22 eIF 2α Phosphorylation 40-50% confluent HeLa cells were seeded in 60 mm dishes and were mock infected or infected with wtVV, VVΔE3L, VVΔE3L/ATV eIF2α at a moi of 5. Six hours post infection (hpi) the cells were scraped into the medium and pelleted by centrifugation at 1000 rpm, 4° C., for 10 minutes. The supernatant was removed and the cell pellet was washed in 1 ml of 1×PBS. The infected cells were then lysed using 100 μl of RIPA buffer (1×PBS, 1% NP-40, 0.5% sodium deoxycholate, 0.1% SIDS and 50 mM sodium fluoride), incubated on ice for 10 minutes and then centrifuged at 10,000 g at 4° C. for 10 minutes. 80 μl of the supernatant was transferred to a fresh microfuge tube containing 80 μl of 2×SDS sample buffer and stored at −80° C. until use in western blot analysis.

Cytoplasmic extracts from the above assay were subjected to SDS PAGE electrophoresis in a 12% polyacrylamide gel at 188 volts for 1 hour. The proteins were transferred to nitrocellulose membrane (Osmonics) at 100 volts for 45 minutes in transfer buffer (10 mM CAPS, pH 11.0, 20% methanol, 14 mM β-ME). The nitrocellulose membrane was blocked for one hour in blotto with milk (20 mM Tris-HCl, pH 7.8, 180 mM NaCl, 3% carnation nonfat dry milk). The blot was incubated overnight at 4° C. with the primary antibody raised in rabbit (1:500 dilution), which recognizes only the phosphorylated form of eIF2 (Research Genetics). The primary antibodies were removed and the blot was washed 3 times with blotto containing milk for 1 hour at room temperature. Then the blot was probed with 1:5000 dilution of goat anti-rabbit IgG-peroxidase conjugate (Sigma). The secondary antibodies were removed and the blot was washed 3 times for 10 minutes each in blotto with milk, and then washed 3 times for 5 minutes each in blotto without milk. The blot was developed by chemiluminiscence.

In response to virus infection, PKR is activated by dsRNA and in turn phosphorylates eIF2α, thus inhibiting protein synthesis. To determine if the recombinant virus can lead to phosphorylation of eIF2α, HeLa cells were mock infected or infected with wtVV, VVΔE3L, VVΔE3L/ATV eIF2α at a moi of 5. Cells were harvested at 6 hpi and the resulting total cell lysates were analyzed by chemiluminiscent western blot as described in Examples 1 and 23. eIF2α was found to be phosphorylated in cells infected with VVΔE3L but not with wtVV or VVΔE3L/ATV eIF2α (FIG. 13).

Example 23

PKR Activation and Inhibition

Virus infection leads to the production of dsRNA in the infected cell. dsRNA is required for the activation of PKR which then becomes autophosphorylated and acts on its substrates. PKR activation can be easily detected by looking for its phosphorylation using a chemiluminiscent western blot.

HeLa cells were seeded at 50% confluency in 60 mm dishes and mock infected or infected with wtVV, VVΔE3L and VVΔE3L/ATV eIF2α at a moi of 5. Cells were harvested at 2, 4 and 6 hpi by scraping cells into the medium and pelleting by centrifugation at 1000 rpm, 4° C., for 10 minutes. The supernatant was removed and the cell pellet was washed in 1 ml of 1×PBS. The infected cells were then lysed using 100 μl of RIPA buffer (1×PBS, 1% NP-40, 0.5% sodium deoxycholate, 0.1% SDS and 50 mM sodium fluoride), incubated on ice for 10 minutes and then centrifuged at 10,000 g at 4° C. for 10 minutes. 80 μl of the supernatant was transferred to a fresh microfuge tube containing 80 μl of 2×SDS sample buffer and stored at −80° C. until use in western blot analysis.

Whole cell extracts were then analyzed for PKR activation by a western blot using anti-PKR antibody which recognizes both phosphorylated and non-phosphorylated PKR. Phosphorylated form is recognized by a shift on the gel as it runs higher compared to the non-phosphorylated form. Whole cell extracts were then run on 10% SDS-PAGE gel, proteins were transferred onto the nitrocellulose membrane and probed with 1:1000 dilution of mouse anti-PKR antibody (Transduction labs). The blot was developed by chemiluminiscence. The same assay was also performed by treating cells with Cytosine β-D arabinofuranoside (AraC, Sigma, 5 mg/ml stock) to a final concentration of 40 μg/ml, one hour prior to the infection. Arac was also added to the inoculum and also to the medium used to overlay HeLa cells after infection. Infected cells were harvested 6 hpi and analyzed in the same way as described above.

Figure 14:
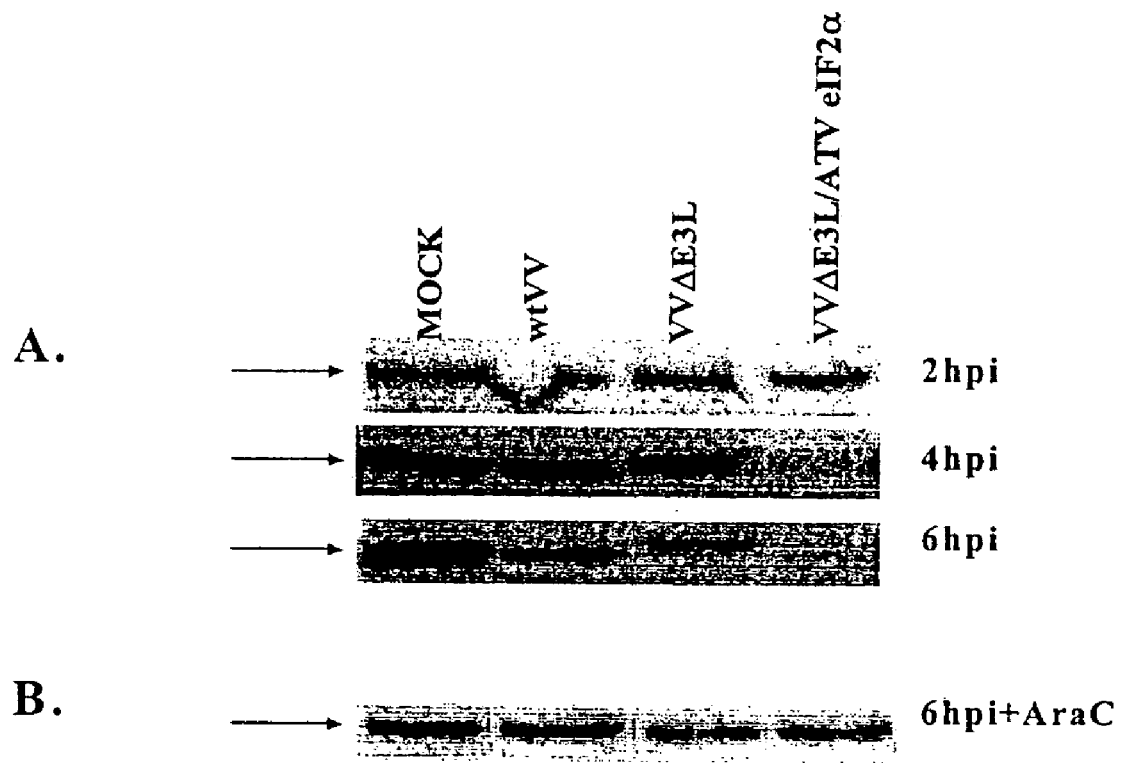
FIG. 14. Western blot analysis to determine the PKR activation. A) HeLa cells were mock infected or infected with wtVV, VVΔE3L, VVΔ3L/ATV eIF2α at a moi of 5 and harvested at 2, 4, and 6 hpi. Whole cell extracts were prepared as described in materials and methods and were run on 10% SDS-PAGE gel. The proteins were transferred to nitrocellulose, probed with anti PKR antibody which recognizes both phosphorylated and unphosphorylated forms of PKR. The blots were assayed by chemiluminiscense. Phosphorylated form of PKR runs little higher on the blot than the unphosphorylated form. B) same as A except that the cells were treated with 40 μg/ml AraC as described in materials and methods. AraC blocks DNA synthesis and therefore dsRNA cannot be formed at late times post infection. The arrows indicate PKR protein.

FIG. 14A shows the results of the assay. Mock shows only non-phosphorylated form of PKR (lane 1 at all time points). Infection with wtVV does not lead to the activation of PKR as E3L gene inhibits PKR activity by sequestering dsRNA and thus shows only the non-phosphorylated form (lane 2 at all time points). Infection with VVΔE3L leads to the activation of PKR as there is no E3L to bind and sequester dsRNA. PKR is not activated at 2 hpi as it has only non-phosphorylated form (lane 3) whereas it gets activated by 4 hpi which is indicated by a shift in the phosphorylated band of PKR although the shift is more prominent at 6 hpi (lane 3).

On the other hand, infection with VVΔE3L/ATV eIF2α leads to the degradation of PKR by 4 hpi (lane 4), thus indicating that somehow the eIF2α homolog is acting as a PKR inhibitor. To determine if this degradation is mediated by dsRNA or not, HeLa cells were pretreated with AraC for one hour prior to infection. AraC inhibits DNA synthesis, thus blocking the formation of dsRNA at late times post infection. Cells were then mock infected or infected with wtVV, VVΔE3L, VVΔE3L/ATV eIF2α at a moi of 5 and harvested at 6 hpi. The cell extracts were then analyzed by western blot following the same procedure as described above for PKR activation. FIG. 14B shows that the PKR is not degraded in VVΔE3L/ATV eIF2α infected cells, thus suggesting that the degradation might be mediated by dsRNA.

Example 24

RNA Degradation

It has been demonstrated that activation of endogenous RNase L or increased production of enzymes in the 2-5A pathway causes degradation of rRNA into characteristic discrete fragments that correlated with apoptosis (Diaz-Guerra et al., *Virology* 227:220-228; Diaz-Guerra et al., 1997, *Virology* 236:354-363). The following assay was performed to investigate the activity of 2-5A pathway in the recombinant virus infected cells.

100 mm dishes with confluent monolayers of S3 HeLa cells from both ATCC and Frederick were mock infected or infected with wtVV, VVΔE3L, VVΔE3L/ATV eIF2α at a moi of 5. 18 hpi cells were scraped into the media and pelleted by centrifugation. The pellets were washed with 1×PBS and pelleted again. After removing all of the supernatant from the pellet, the cells were resuspended in 500 μl of RNase-free Tris-buffered saline (TBS) and immediately followed by 1:1 phenol: chloroform extraction. The sample was centrifuged for 10 minutes at 4° C. at 10,000 rpm. The top layer was transferred to a sterile eppendorf tube and a 1:1 dilution of chloroform:isoamyl alcohol was added. The samples were again centrifuged and the top layer was transferred into a sterile eppendorf tube. The samples were then treated with 1/10 volume of DEPC treated 3 M sodium acetate, pH 5.0 and then 2.5 volumes of ethanol was added. The RNA was allowed to precipitate for 30 minutes at −80° C. The samples were centrifuged at 10,000 rpm, 4° C. for 30 minutes to pellet the RNA. The RNA pellet was dried and resuspended in 20 μl of 0.5% SDS-DEPC water. For analysis, denatured RNA was fractionated on 1.8% formaldehyde-agarose gels and stained using ethidium bromide buffer.

Figure 15:
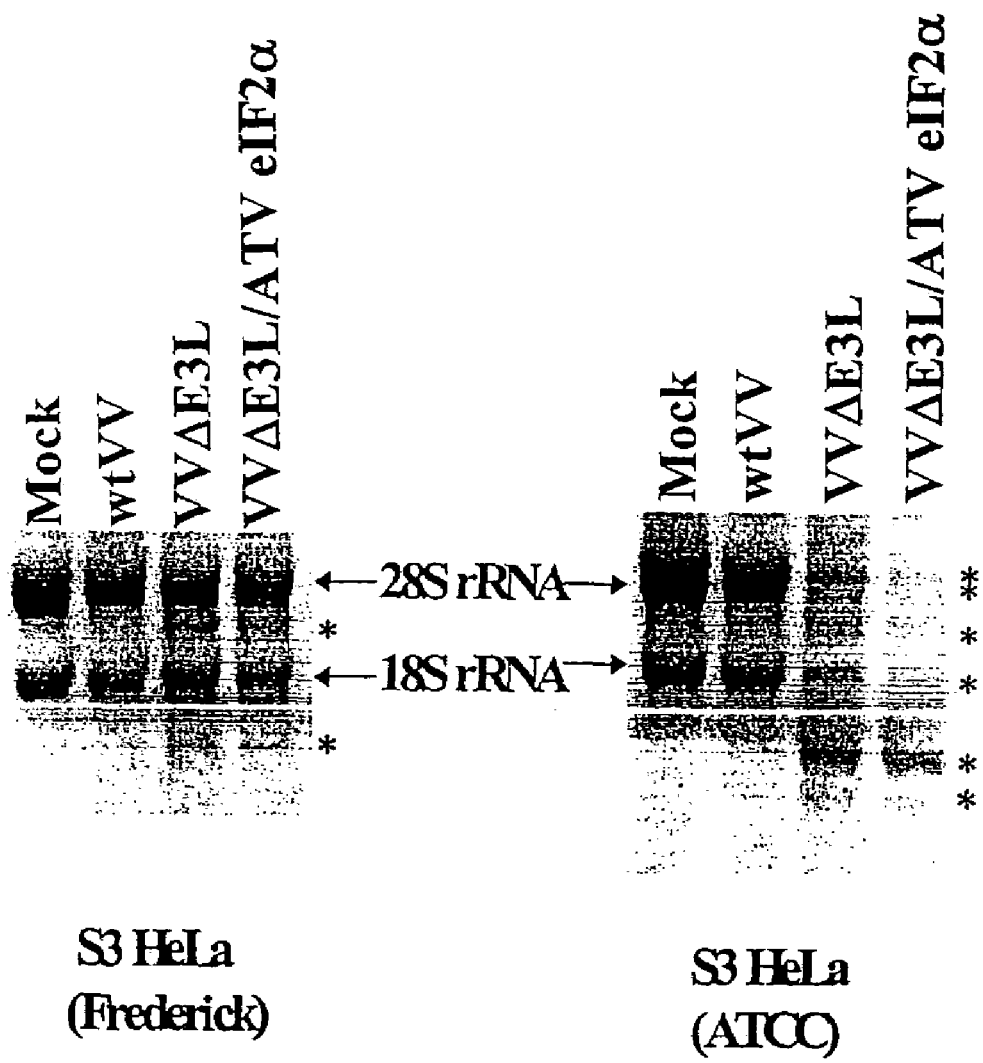
FIG. 15. RNA degradation assay. HeLa and S3 HeLa cells were mock infected or infected with wtVV, VVΔE3L, VVΔE3L/ATV eIF2α at a moi of 5 and harvested at 18 hpi. RNA was extracted as described in materials and methods and fractionated on 1.8% formaldehyde-agarose gels and stained using ethidium bromide buffer. Stars indicate degraded RNA products.

Equal amounts of RNA were fractionated in 1.8% agarose-formaldehyde gels as shown in FIG. 15. No fragmentation of RNA was observed in mock or wtVV infected cells in either cell line, indicating that the 2-5A pathway is inhibited in wtVV infected cells (lanes 1 and 2). Infection with VVΔE3L and VVΔE3L/ATV eIF2α leads to the fragmentation of rRNA indicative of activation of the 2-5A pathway in both the cell lines (lanes 3 and 4), although the pathway is more active in S3 HeLa cells from ATCC.

Example 25

Single Step Growth Curve

Single step growth curves were performed in HeLa cells. HeLa cells were seeded at 80% confluency in 60 mm dishes and infected with wtVV, VVΔE3L and VVΔE3L/ATV eIF2α at a moi of 5. After one hour, the inoculum was removed by washing cells with 1×PBS and overlaid with complete HeLa media. Cells were harvested at 0 hpi and 30 hpi by scraping cells into the media and pelleting down by centrifugation at 1000 rpm, 4° C. for 10 minutes. The pellet was resuspended in 200 μl of 1 mM Tris HCl, pH 8.8 and subjected to three rounds of freeze thaws. The resultant virus was titered in RK-13 cells.

Figure 16:
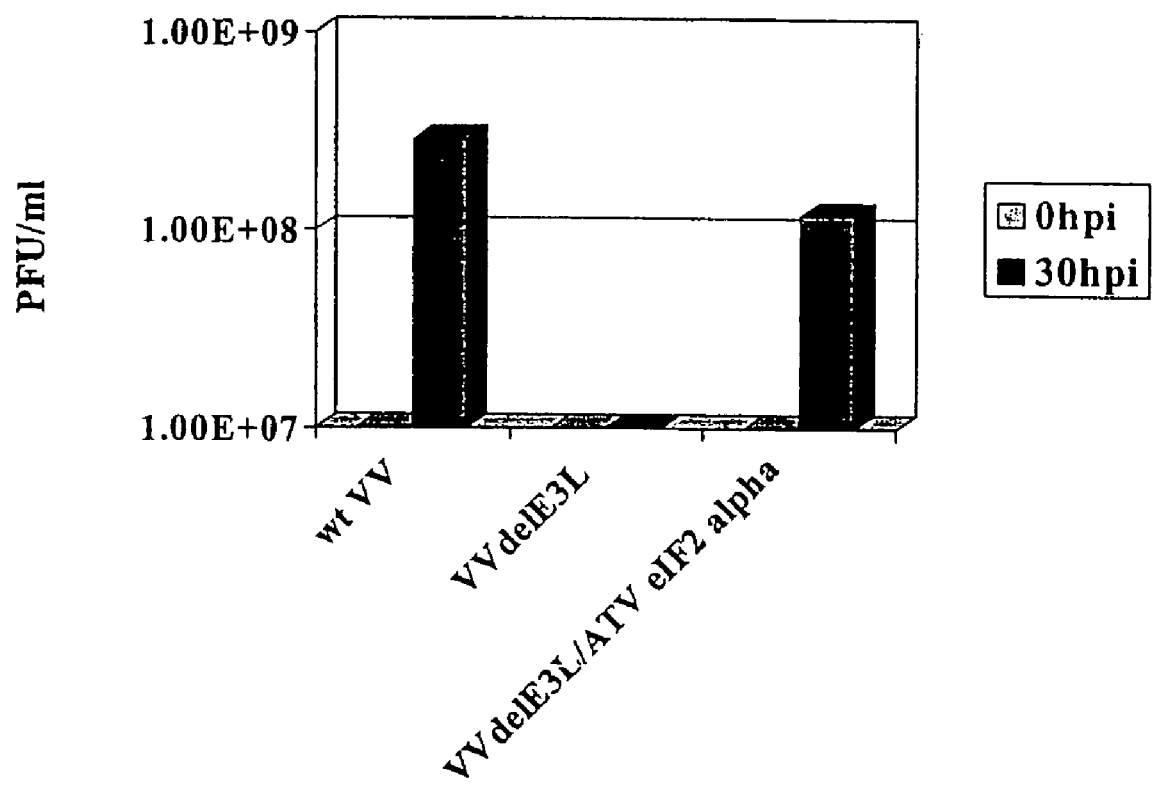
FIG. 16. Single step growth curve. HeLa cells were infected with wtVV, VVΔE3L, or VVΔ3L/ATV eIF2α at a moi of 5 and harvested at 0 and 30 hpi. The cell pellet was freeze thawed to release the virus from the cells as described in materials and methods. The resultant virus was titered in RK-13 cells and plotted as above with the titer expressed as PFU/ml on the Y-axis and the virus on the X-axis.

As shown in FIG. 16, VVΔE3L did not replicate in HeLa cells in agreement with the results obtained under plaque assay conditions (Table 1). On the other hand, VVΔE3L/ATV eIF2α was able to replicate in HeLa cells almost to the same extent of wtVV, in contrast to the results obtained in the plaque assay (Table 1). Thus under single cycle conditions the recombinant virus was able to replicate normally in the infected cells. This led to assays to determine how the virus behaves under multi-cycle conditions, which reveal whether the virus is being released from the infected cell and whether it is spreading to the neighboring cells.

Example 26

Multi-Step Growth Curve

HeLa cells were seeded at 50% confluency in 60 mm dishes and infected with wtVV, VVΔE3L and VVΔE3L/ATV eIF2α at a moi of 0.01. After one hour, the inoculum was removed by washing cells with 1×PBS and overlaid with complete HeLa media. Cells were harvested at 0 hpi and 72 hpi by scraping cells into the media and pelleting down by centrifugation at 1000 rpm, 4° C. for 10 minutes. The supernatant was saved and the pellet was resuspended in 200 μl of 1 mM Tris HCl, pH 8.8 and subjected to three rounds of freeze thaws. The resultant virus was titered in RK-13 cells.

Figure 17:
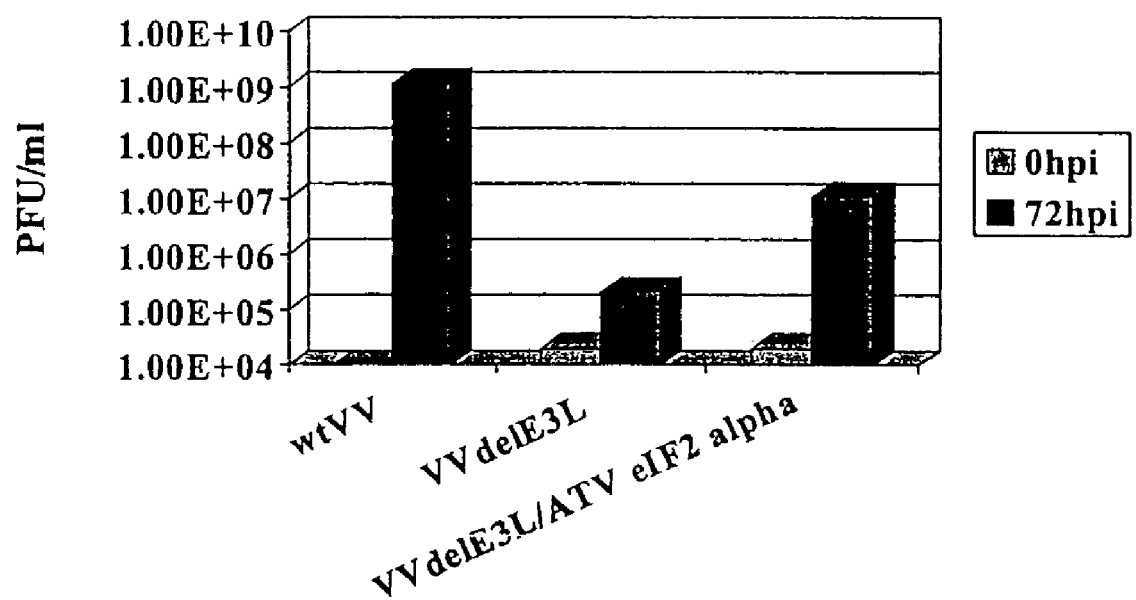
FIG. 17. Multi-step growth curve. HeLa cells were infected with wtVV, VVΔE3L, VVΔ3L/ATV eIF2α at a moi of 0.01 and harvested at 0 and 72 hpi. The cell pellet was freeze thawed to release the virus from the cells as described in materials and methods. The resultant virus was titered in RK-13 cells and plotted as above with the virus titer expressed as PFU/ml on the Y-axis and the virus on the X-axis.

As shown in FIG. 17, the recombinant virus was unable to grow as well as wtVV under multi-cycle conditions. The cultured supernatant from these infected cells was also tested for viral release from the infected cells and it has been found that the recombinant virus was getting released into the media from the infected cell (data not shown). Thus, productive secondary infections of the virus are somehow inhibited and, therefore, the virus is unable to plaque in HeLa cells (Table 1). This is probably due to the induction of IFN in the infected cell which is then secreted out into the media and is thus responsible for inhibiting productive secondary infections of the virus.

Example 27

Rescue of VSV—IFN Induction

One way to test for IFN induction is to treat HeLa cells with the cultured supernatant from the multi-step growth curve (Example 26) along with the presence or absence of anti IFN-β antibody and then infect those cells with Vesicular Stomatitis Virus (VSV). The rationale behind this is, since VSV is IFN sensitive, it should not grow in the supernatant-treated cells if there is IFN present in that supernatant. Conversely, VSV should grow in those cells which have anti IFN-β antibody along with the cultured supernatant.

Sub confluent HeLa cells were mock treated or treated with the cultured supernatant from the above multi-step growth curve in the presence or absence of 3000 neutralization units of human anti IFN-β antibody (Calbiochem). 16 hours post treatment, cells were infected with 100 pfu of Vesicular Stomatitis Virus (VSV). After one hour the cells were overlaid with 1.5% agarose supplemented with complete 2×MEM media. 24 hours later cells were overlaid with 1.5% agarose supplemented with complete 2×MEM media containing neutral red solution (1.5 ml of a 3.33 g/L solution (GIBCO) per 50 ml of medium) and 6 hours later the number of plaques of VSV were counted.

It is evident from FIG. 18, that IFN is present in the cultured supernatant from the recombinant virus infected cells and, therefore, VSV was not able to grow in those cells. Growth of VSV was rescued in those cells where anti IFN-β antibody has neutralized all the IFN present in the cultured supernatant. This argues that IFN is being induced in VVΔE3L/ATV eIF2α infected cells.

Example 28

Sub-Cellular Fractionation for IRF-3 Phosphorylation

Another way to test for IFN induction is to look for IRF-3 phosphorylation. IRF-3 is a transcription factor that is activated upon virus infection by phosphorylation (Lin et al., 1998, *Mol Cell Biol* 19:2986-96; Sato et al.; 1998, *FEBS Lett* 452:112-16; Weaver et al., 1998, *Mol Cell Biol* 18:1359-68; Yoneyama et al., 1998, *EMBO J* 17:1087-95), translocates to the nucleus (Sato et al., 1998, *FEBS Lett* 452:112-16; Yoneyama et al., 1998, *EMBO J* 17:1087-95) and leads to the induction of IFN-α and IFN-β genes (Juang et al., 1998, *Proc Natl Acad Sci USA* 95:9837-42; Sato et al., 1998, *FEBS Lett* 452:112-16; Schafer et al., 1998, *J Biol Chem* 273:2714-20; Yoneyama et al., 1998, *EMBO J.* 17:1087-95).

HeLa cells were seeded at 80% confluency in 100 mm dishes and infected with wtVV, VVΔE3L and VVΔE3L/ATV eIF2α at a moi of 5. Cells were harvested at 6 hpi and nuclear extracts were prepared as described elsewhere (Servant et al., 2001, *J Biol Chem* 276(1):355-63). The extracts were then run on 10% SDS-PAGE gel, proteins were transferred onto the nitrocellulose membrane and probed with rabbit anti-IRF-3 antibody (kindly provided by Dr. Michael David, University of California at San Diego). The western blot was developed by chemiluminiscence.

IRF-3 was detected in the nucleus only in VVΔE3L and VVΔE3L/ATV eIF2α infected cells but not in mock or wtVV infected cells (FIG. 19), indicating that the recombinant virus leads to the activation of IRF-3, which then subsequently translocates to the nucleus and leads to the induction of IFN-β.

Example 29

Weight Loss on Challenging Mice Vaccinated with VVΔE3L/ATV eIF2α

4 male C57BL/6 mice were immunized with different doses (ranging from 2 to 5,000 plaque forming units) of recombinant vaccinia virus with ATV eIF2α homolog in place of its E3L and with 1000 pfu's of VVΔE3L. One month later the immunized mice and the unimmunized controls (mock) were challenged with a $10^6$ pfu of wt VV. Weight loss was used as an indicator of disease due to wt VV. Severe weight loss was observed in the unimmunized control. Weight loss of mice vaccinated with 2 and 20 pfu of VVΔE3L/ATV eIF2α was not significantly different from mock-vaccinated mice challenged with wt VV but both 300 and 5000 pfu were significantly different (FIG. 20). Therefore vaccination with 300 pfu of VVΔE3L/ATV eIF2α was sufficient to protect against wt VV challenge.

Example 30

Survival of Mice Following Intranasal Infection with VVΔE3L/ATV eIF2α

Four C57BL/6 mice were infected with each dilution of VVΔE3L/ATV eIF2α and $10^4$ dilution of wt VV as indicated in the figure. Deaths were recorded. The LD50 of wt VV was observed on day 9 post infection. The LD50 of VVΔE3L/ATV eIF2α could not be calculated as even the highest dose did not kill 50% of the mice (FIG. 21).

Example 31

Similarity Between ATV eIF2 α and Vaccinia Viral E3L and K3L

The present invention relates, in part, to experiments directed to elucidating the role of the eIF2α homolog from ATV, a member of the genus *Ranavirus*, family Iridoviridae. Several isolates exhibit a gene encoding a protein with homology to eukaryotic eIF-2α and the corresponding VV protein, K3L (Essbauer et al., 2001, *Virus Genes* 23(3):347-59). eIF2α homolog from ATV has 35% identity with and 55% similarity to the human eIF2α protein and 30% identity with and 51% similarity to the K3L protein of vaccinia virus. Its N-terminus shows significant homology to the amino terminus of human eIF2α protein and to the full length K3L protein. K3L of VV binds to PKR as a pseudosubstrate (Sharp et al., 1997, *Eur J Biochem* 250(1):85-91) and acts as an inhibitor of PKR. Since a high sequence similarity exists between K3L and eIF2α homolog, the latter could potentially act as a PKR inhibitor.

Example 32

Vector System Selection

A vaccinia virus system was chosen to characterize eIF2α homolog from ATV. VV is a useful recombinant vector as it is easy to delete and insert genes from its genome. The E3L gene of VV confers the interferon resistance phenotype to the virus. So VV deleted of the E3L gene has turned out to be an excellent system for in vivo analysis of function of exogenous proteins (Jacobs et al., 1998, *Methods: A comparison to methods in enzymology* 15:225-232). Insertion of ATV eIF2α homolog into the E3L locus of VV allows its ability to regulate the IFN response to be examined. Even though ATV eIF2α is homologous to K3L of VV, it was the E3L gene of VV that was replaced with ATV eIF2α homolog because the phenotypic characteristics of VVΔE3L are more readily observable and allow examination the entire IFN response. The results of this work established that the eIF2α homolog from iridoviruses acts a novel inhibitor of PKR by leading to its proteolytic degradation.

Example 33

Possible Mechanism of Action for ATV eIF2α

Nothing in this example should be construed to limit the scope of the invention. Rather, this example is provided merely to illustrate further aspects that are within the contemplation of the invention.

Poliovirus infection leads to the degradation of PKR and degradation requires both an RNA and protein component. Poliovirus infected cell extracts pretreated with trypsin, RNase A, or RNase III were no longer able to degrade PKR, suggesting that a protein and an RNA component with both single-stranded and double-stranded characteristics was required for PKR degradation (Black et al., 1993, *J Virol* 67(2), 791-800). By in vitro experiments, it was also shown that kinase activation was not a prerequisite for the degradation of PKR by poliovirus and that preincubation with dsRNA could block the poliovirus-mediated degradation of PKR (Black et al., 1993, *J Virol* 67(2), 791-800). The evidence suggests that a similar phenomenon must be occurring in VVΔE3L/ATV eIF2α, infected cells by which the eIF2α homolog is able to induce the degradation of PKR and this degradation might be mediated by dsRNA. As proposed by Black et al., 1993 (*J Virol* 67(2), 791-800), it is possible that in Poliovirus infected cells, PKR undergoes some conformational change upon interaction with dsRNA and this alteration in structure then enables a cellular protease to degrade the kinase or alternatively, the dsRNA and protease act in concert, possibly as a ribonucleoprotein complex, to proteolyze the kinase directly and completely. It is interesting to note that the Ranaviruses with an eIF2α homolog might regulate PKR by a similar mechanism.

Cellular protein synthesis is reduced in FV-3 (type species of the genus Ranavirus) infected fish cells and phosphorylation of the a subunit of eIF2 has been observed in these infected cells thus suggesting that translational shut-off may be due to activation of a kinase that selectively phosphorylates eIF2α (Chinchar and Dholakia, 1989, *Virus Res* 14(3): 207-23). While selectively blocking host cell translation, FV-3 can synthesize more than 60 virus-specific polypeptides (Chinchar and Yu, 1990, *Virus Res* 16(2):163-74). These results suggest that the selective translation of FV-3 messages in virus-infected cells may partly be due to the higher translational efficiency of viral messages.

IRF3/7 activation can be stimulated by dsRNA and a novel cellular kinase distinct from PKR is responsible for its phosphorylation. E3L protein of VV exerts its anti-IFN effect by inhibiting not only PKR but also the distinct IRF3/7 kinase(s) (Smith et al., 2001, *J Biol Chem* 276(12):8951-7). While wtVV inhibits IRF-3 phosphorylation, infection with VVΔE3L leads to its phosphorylation. Infection with VVΔE3L/ATV eIF2α also leads to the phosphorylation of IRF-3 suggesting that the ATV eIF2α homolog is not able to inhibit the induction of IFN. Translocation of IRF-3 to the nucleus was seen even in the absence of PKR in VVΔE3L/ATV eIF2α infected cells, supporting the data that PKR is not the kinase responsible for phosphorylating IRF-3.

To test for the anti-IFN activity of iridoviral eIF2α, chicken embryo fibroblast (CEC-32) cells were transfected with iridoviral eIF2α and then infected with VSV (Essbauer et al., 2001, *Virus Genes* 23(3):347-59). Their results found no significant differences between the viability of control cells and eIF2α transfected CEC-32 cells. Also, their attempts to counteract the antiviral effects of chicken IFN by iridoviral eIF2α have failed. The results indicate that the ATV eIF2α can partially counteract the antiviral effects of mammalian IFN by inhibiting PKR. It is possible that the ATV eIF2α homolog is able to recognize mammalian PKR, suggesting the presence of a PKR-like enzyme in salamanders. Subsequently, ATV eIF2α might be involved in evading host defenses in salamanders.

Even though the eIF2α homolog is homologous to K3L of VV, the homolog has a better effect than K3L as the recombinant virus was able to partially rescue VVΔE3L. Since the C-terminus of the homolog has no homology to any known protein, further work is needed to explore the function of the C-terminus. Since K3L binds to PKR and acts as a pseudosubstrate, it would be interesting to see if the homolog can also interact directly with PKR. KGYID (amino acids 73-78 of SEQ ID NO:2), the motif required for interaction of K3L with PKR (Kawagishi et al., 1997, *Mol Cell Biol* 17(7):4146-58; Kawagishi et al., 2000, *Virology* 276(2):424-34; Sharp et al., 1997, *Eur J Biochem* 250(1):85-91) is modified to KGYVD (amino acids 81-85 of SEQ ID NO: 1) in all iridoviral eIF2α proteins. This modification may have an effect on the possible interaction of eIF2α homolog with PKR.

The results suggest that the salamander virus ATV contains a novel gene that may counteract host defenses, emphasizing that there is an evolutionary significance in obtaining this gene in its genome. Since the eIF2α homolog was able to inhibit part of the mammalian IFN system, salamanders may have an antiviral state similar to mammals.

What is claimed is:

1. A recombinant vaccinia virus comprising a nucleic acid encoding the amino acid sequence of SEQ ID NO: 1.

2. A recombinant vaccinia virus lacking at least a portion of the vaccinia E3L gene and comprising a nucleic acid encoding the amino acid sequence of SEQ ID NO:1.

3. The recombinant vaccinia virus of claim 2, wherein the vaccinia E3L gene is deleted and the nucleic acid encoding the amino acid sequence of SEQ ID NO: 1 is inserted in its place.

4. A vaccine produced using the recombinant virus of any one of claims 1, 2 or 3.

5. A method of stimulating a mammal to produce antiviral antibodies comprising contacting the mammal with a recombinant vaccinia virus of any one of claims 1, 2 or 3.

6. An expression vector comprising the recombinant vaccinia virus of any one of claims 1, 2 or 3 wherein said vector further comprises exogenous DNA operably linked to regulatory elements that control expression of said exogenous DNA.

* * * * *

SEQUENCE LISTING

```
<160> NUMBER OF SEQ ID NOS: 7

<210> SEQ ID NO 1
<211> LENGTH: 259
<212> TYPE: PRT
<213> ORGANISM: ATV eIF2_alpha
<220> FEATURE:
<221> NAME/KEY: SITE
<222> LOCATION: (0)...(0)
<223> OTHER INFORMATION: ATV eIF2_alpha
```

-continued

<400> SEQUENCE: 1

```
Met Ala His Asn Arg Phe Tyr Ser Glu Ile Leu Pro Lys Gln Gly Asp
 1               5                  10                  15

Val Thr Met Cys Arg Val Leu Ser Gln Ser Asp Ser Trp Asp Glu Gly
            20                  25                  30

Val Tyr Val Ser Met Met Glu Tyr Gly Asn Val Lys Gly Tyr Val Ala
        35                  40                  45

Ile Gly Val Glu Asn His Arg Asp Ile Arg Lys Arg Phe Arg Lys Leu
    50                  55                  60

Ala Pro Gly Ala Glu Met Cys Met Thr Val Leu Arg Val Asp Arg Glu
65                  70                  75                  80

Lys Gly Tyr Val Asp Leu Asp Asp Arg Pro Val Asn Ser Asn Gln Ala
                85                  90                  95

Tyr Glu Cys Cys Ser Arg Tyr Gln Leu Arg Arg Thr Glu Met Ala Val
            100                 105                 110

Ala Glu Arg Ala Ala Glu Tyr Ala Gly Val Lys Gly Ser Ala Val Tyr
        115                 120                 125

Asp Phe Leu Asp Glu Thr Val Arg Ala Leu Ile Pro Gly Ser Leu Met
    130                 135                 140

Ser Gly Thr Lys Gly Leu Lys Ile Ser Ser Asp Leu Lys Gln Leu Leu
145                 150                 155                 160

Lys Glu Phe Gly Ala Glu Val Gly Leu Asp Arg Ala Gly Arg Ala Glu
                165                 170                 175

Ala Val Val Arg Val Pro Gly Ala Phe Phe Gly His Val Leu Arg Gly
            180                 185                 190

Val Thr Asn Ala Tyr Asp Ala Met Lys Glu Met Lys Pro Asp Ser Gly
        195                 200                 205

Val Asn Val Ala Val Tyr Pro Pro Glu Arg Gly Val Val Ala Val Thr
    210                 215                 220

Val Met Ala Gly Asp Ser Glu Ala Ala Tyr Trp Gly Leu His Ala Val
225                 230                 235                 240

Leu Phe Lys Val Arg Glu Val Val Lys Ala Ala Gly Gly Gly Leu Cys
                245                 250                 255

Pro Phe Val
```

<210> SEQ ID NO 2
<211> LENGTH: 88
<212> TYPE: PRT
<213> ORGANISM: vaccinia virus K3L
<220> FEATURE:
<221> NAME/KEY: SITE
<222> LOCATION: (0)...(0)
<223> OTHER INFORMATION: vaccinia virus K3L

<400> SEQUENCE: 2

```
Met Leu Ala Phe Cys Tyr Ser Leu Pro Asn Ala Gly Asp Val Ile Lys
 1               5                  10                  15

Gly Arg Val Tyr Glu Lys Asp Tyr Ala Leu Tyr Ile Tyr Leu Phe Asp
            20                  25                  30

Tyr Pro His Ser Glu Ala Ile Leu Ala Glu Ser Val Lys Met His Met
        35                  40                  45

Asp Arg Tyr Val Glu Tyr Arg Asp Lys Leu Val Gly Lys Thr Val Lys
    50                  55                  60

Val Lys Val Ile Arg Val Asp Tyr Thr Lys Gly Tyr Ile Asp Val Asn
65                  70                  75                  80
```

Tyr Lys Arg Met Cys Arg His Gln
                85

<210> SEQ ID NO 3
<211> LENGTH: 315
<212> TYPE: PRT
<213> ORGANISM: Homo sapien
<220> FEATURE:
<221> NAME/KEY: SITE
<222> LOCATION: (0)...(0)
<223> OTHER INFORMATION: human eIF2_alpha

<400> SEQUENCE: 3

Met Pro Gly Leu Ser Cys Arg Phe Tyr Gln His Lys Phe Pro Glu Val
1               5                   10                  15
Glu Asp Val Val Met Val Asn Val Arg Ser Ile Ala Glu Met Gly Ala
            20                  25                  30
Tyr Val Ser Leu Leu Glu Tyr Asn Asn Ile Glu Gly Met Ile Leu Leu
        35                  40                  45
Ser Glu Leu Ser Arg Arg Arg Ile Arg Ser Ile Asn Lys Leu Ile Arg
    50                  55                  60
Ile Gly Arg Asn Glu Cys Val Val Val Ile Arg Val Asp Lys Glu Lys
65                  70                  75                  80
Gly Tyr Ile Asp Leu Ser Lys Arg Arg Val Ser Pro Glu Glu Ala Ile
                85                  90                  95
Lys Cys Glu Asp Lys Phe Thr Lys Ser Lys Thr Val Tyr Ser Ile Leu
            100                 105                 110
Arg His Val Ala Glu Val Leu Glu Tyr Thr Lys Asp Glu Gln Leu Glu
        115                 120                 125
Ser Leu Phe Gln Arg Thr Ala Trp Val Phe Asp Asp Lys Tyr Lys Arg
    130                 135                 140
Pro Gly Tyr Gly Ala Tyr Asp Ala Phe Lys His Ala Val Ser Asp Pro
145                 150                 155                 160
Ser Ile Leu Asp Ser Leu Asp Leu Asn Glu Asp Glu Arg Glu Val Leu
                165                 170                 175
Ile Asn Asn Ile Asn Arg Arg Leu Thr Pro Gln Ala Val Lys Ile Arg
            180                 185                 190
Ala Asp Ile Glu Val Ala Cys Tyr Gly Tyr Glu Gly Ile Asp Ala Val
        195                 200                 205
Lys Glu Ala Leu Arg Ala Gly Leu Asn Cys Ser Thr Glu Asn Met Pro
    210                 215                 220
Ile Lys Ile Asn Leu Ile Ala Pro Pro Arg Tyr Val Met Thr Thr Thr
225                 230                 235                 240
Thr Leu Glu Arg Thr Glu Gly Leu Ser Val Leu Ser Gln Ala Met Ala
                245                 250                 255
Val Ile Lys Glu Lys Ile Glu Glu Lys Arg Gly Val Phe Asn Val Gln
            260                 265                 270
Met Glu Pro Lys Val Val Thr Asp Thr Asp Glu Thr Glu Leu Ala Arg
        275                 280                 285
Gln Met Glu Arg Leu Glu Arg Glu Asn Ala Glu Val Asp Gly Asp Asp
    290                 295                 300
Asp Ala Glu Glu Met Glu Ala Lys Ala Glu Asp
305                 310                 315

<210> SEQ ID NO 4
<211> LENGTH: 36
<212> TYPE: DNA

-continued

```
<213> ORGANISM: Artificial Sequence
<220> FEATURE:
<223> OTHER INFORMATION: sense eIF2_alpha oligonucleotide

<400> SEQUENCE: 4
attaggatcc gccatggcac acaacaggtt ttacag                                36

<210> SEQ ID NO 5
<211> LENGTH: 33
<212> TYPE: DNA
<213> ORGANISM: Artificial Sequence
<220> FEATURE:
<223> OTHER INFORMATION: antisense eIF2_alpha oligonucleotide

<400> SEQUENCE: 5
attagtcgac atatcacaca aaggggcaca gtc                                   33

<210> SEQ ID NO 6
<211> LENGTH: 17
<212> TYPE: DNA
<213> ORGANISM: Artificial Sequence
<220> FEATURE:
<223> OTHER INFORMATION: sense ATV  (Ambystoma Tigrinum Virus)
      eIF2_alpha oligonucleotide

<400> SEQUENCE: 6
cgaaccacca gaggatg                                                     17

<210> SEQ ID NO 7
<211> LENGTH: 21
<212> TYPE: DNA
<213> ORGANISM: Artificial Sequence
<220> FEATURE:
<223> OTHER INFORMATION: antisense ATV (Ambystoma Tigrinum Virus)
      eIF2_alpha oligonucleotide

<400> SEQUENCE: 7
tagtcgcgtt aatagtacta c                                                21
```